(12) United States Patent  
Bowen et al.

(10) Patent No.: US 8,168,657 B2
(45) Date of Patent: May 1, 2012

(54) SOLENOPSIN A, B AND ANALOGS AND AS NOVEL ANGIOGENESIS INHIBITORS

(76) Inventors: J. Phillip Bowen, Hull, GA (US); Jack L. Arbiser, Atlanta, GA (US); David Whitmire, Atlanta, GA (US); M. Scott Furness, Bethesda, MD (US)

( * ) Notice: Subject to any disclaimer, the term of this patent is extended or adjusted under 35 U.S.C. 154(b) by 1403 days.

(21) Appl. No.: 10/502,080

(22) PCT Filed: Jan. 24, 2003

(86) PCT No.: PCT/US03/02105
§ 371 (c)(1),
(2), (4) Date: Oct. 8, 2004

(87) PCT Pub. No.: WO03/061598
PCT Pub. Date: Jul. 31, 2003

(65) Prior Publication Data
US 2005/0038071 A1 Feb. 17, 2005

Related U.S. Application Data

(60) Provisional application No. 60/351,880, filed on Jan. 25, 2002.

(51) Int. Cl.
*A61K 31/445* (2006.01)
(52) U.S. Cl. ........................................ 514/315
(58) Field of Classification Search .......... 514/315
See application file for complete search history.

(56) References Cited

U.S. PATENT DOCUMENTS

| | | | |
|---|---|---|---|
| 4,910,209 A * | 3/1990 | Rehmert, Jr. | 514/315 |
| 5,075,320 A | 12/1991 | Rehmert, Jr. | |
| 5,098,914 A | 3/1992 | Rehmert, Jr. | |
| 5,849,764 A * | 12/1998 | Goulet et al. | 514/337 |
| 6,072,085 A | 6/2000 | Verdaguer et al. | |
| 6,147,059 A * | 11/2000 | Falk et al. | 514/54 |
| 6,362,009 B1 | 3/2002 | Munoz et al. | |
| 6,369,078 B1 * | 4/2002 | Bowen et al. | 514/315 |
| 6,538,144 B2 | 3/2003 | Heitsch | |
| 6,984,660 B2 | 1/2006 | Heitsch | |

OTHER PUBLICATIONS

Arbiser et al., Blood, 2007, 109(2), pp. 560-565.*
Gleich et al., Anticancer Research, 1998, 18(4A), pp. 2607-2609.*
Calabresi et al. In "Goodman & Gilman's The Pharmacological Basis of Therapeutics", 10th Edition, McGraw Hill, 2001, pp. 1381-1385.*
Knowling et al., Invest. New Drugs, 2006, 24, pp. 435-439.*
Kondapaka et al., Mol. Cancer Ther., 2003, 2, pp. 1093-1103.*
Sosman et al., Clin. Cancer Res., 2006, 12(7), pp. 2376s-2383s.*
Johnson et al., British J. Cancer, 2001, 84(10), pp. 1424-1431.*
Voskoglou-Nomikos et al., CLin. Can. Res., 2003, 9, pp. 4227-4239.*
Suggitt et al., Clin. Can. Res., 2005, 11, pp. 971-981.*

(Continued)

*Primary Examiner* — Brandon Fetterolf
*Assistant Examiner* — Paul Zarek
(74) *Attorney, Agent, or Firm* — Henry D. Coleman; R. Neil Sudol; William J. Sapone

(57) ABSTRACT

The present invention relates to solenopsin A and its analogs for use as angiogenesis inhibitors. The present compounds unexpectedly exhibit good activity as angiogenesis inhibitors, which find use as antitumor/anticancer agents as well as to treat a number of conditions or disease states in which angiogenesis is a factor.

11 Claims, 5 Drawing Sheets

OTHER PUBLICATIONS

Arbiser JL, Panigrathy D, Klauber N, Rupnick M, Flynn E, Udagawa T, D'Amato RJ. The antiangiogenic agents TNP-470 and 2-methoxyestradiol inhibit the growth of angiosarcoma in mice. J Am Acad Dermatol. Jun. 1999;40(6 Pt 1):925-9.*

FDA. FDA begins process to remove breast cancer indication from Avastin label., Dec. 2010.*

Yanase T, Tamura M, Fujita K, Kodama S, Tanaka K. Inhibitory effect of angiogenesis inhibitor TNP-470 on tumor growth and metastasis of human cell lines in vitro and in vivo. Cancer Res. Jun. 1, 1993;53(11):2566-70.*

Database HCAPLUS on STN, No. 1973-92973, Jouvenaz et al. "Antibacterial Activity of Venom Alkaloids from the Imported Fire Ant, *Solenopsis invicta*." Abstract, Antimicrobial Agents and Chemotherapy, 1972, vol. 2, No. 4, pp. 191-193.

Johnson JI et al., Relationships between drug activity in NCI preclinical in vitro and in vivo models and early clinical trials. British Journal of Cancer 2001, 84(10):1424-1431.

Liu B et al., Pro-angiogenic effect of IFNgamma is dependent on the PI3K/mTOR/translational pathway in human retinal pigmented epithelial cells. Mol. Vis. 2010, 16:184-193.

Phung TL et al., Endothelial Akt signaling is rate-limiting for rapamycin inhibition of mouse mammary tumor progression. Cancer Res. 2007, 67(11):5070-5075. Erratum in: Cancer Res. 2007, 67(13):6528.

Suggitt M et al., Fifty years of preclinical anticancer drug screening: empirical to target-driven approaches. Clinical Cancer Research 2005, 11:971-981.

Tarnawski AS et al., PTEN silencing reverses aging-related impairment of angiogenesis in microvascular endothelial cells. Biochem Biophys Res Commun 2010, 394(2):291-296.

Voskoglou-Nomikos T et al., Clinical predictive value of the in vitro cell line, human xenograft, and mouse allograft preclinical cancer models. Clinical Cancer Research 2003, 9:4227-4239.

Wang D et al., Induction of vascular endothelial growth factor expression in endothelial cells by platelet-derived growth factor through the activation of phosphatidylinositol 3-kinase. Cancer Res. 1999, 59(7):1464-1472.

Zhong H et al., Modulation of hypoxia-inducible factor 1alpha expression by the epidermal growth factor/phosphatidylinositol 3-kinase/PTEN/AKT/FRAP pathway in human prostate cancer cells: implications for tumor angiogenesis and therapeutics. Cancer Res. 2000, 60(6):1541-1545.

* cited by examiner

R¹ or R² =

SCHEME I

SCHEME II

SOLENOPSIN A, B AND ANALOGS AND AS NOVEL ANGIOGENESIS INHIBITORS

FIELD OF THE INVENTION

The present invention relates to solenopsin A and its analogs for use as angiogenesis inhibitors. The present compounds exhibit unexpected activity as angiogenesis inhibitors, which find use as antitumor/anticancer agents as well as to treat a number of conditions or disease states in which angiogenesis is a factor.

BACKGROUND OF THE INVENTION

The present invention relates to the use of solenopsin A and its analogs as angiogenesis inhibitors.

Angiogenesis may be defined as the development of a blood supply to a given area of tissue. The development of a blood supply may be part of normal embryonic development, represent the revascularization of a wound bed, or involve the stimulation of vessel growth by inflammatory or malignant cells. Sometimes angiogenesis is defined as the process through which tumors or inflammatory conditions derive or create a blood supply through the generation of microvessels. Although it may seem unremarkable that new growth of soft tissue requires new vascularization, the concept of angiogenesis as a key component of tissue growth and in particular, a key point of intervention in pathological tissue growth, had initially met with skepticism. By now the idea is well accepted.

Tumors need to induce formation of blood vessels to grow beyond a small size. A small tumor can use diffusion from nearby capillaries as its source of oxygenation, nutrition, and waste removal. However, once a tumor exceeds a critical mass, the center of the tumor becomes necrotic, because these crucial functions are no longer available. When a tumor gains the ability to generate new blood vessels, perfusion of a larger tumor mass is possible. The ability of malignant cells to form a large tumor and to metastasize is accompanied by decreased cellular differentiation and increased ability to produce angiogenic factors, which results in greater vascularization. There is therefore a strong interest in compounds that block angiogenesis and interrupt the growth process of malignant tumors, inflammatory lesions and benign neoplasms, as well as in compounds which stimulate cellular differentiation, and impede metastasis.

A tumor's ability to become neovascularized permits rapid tumor growth and increases the likelihood of metastases; the transition from a quiescent tumor to an invasive tumor is accompanied by the crucial acquisition of angiogenic properties. The critical point may be characterized as the activation of a specific angiogenic switch. The phenotypic change from quiescence to virulence likely requires a change in the balance of angiogenic simulators and angiogenic inhibitors. The nature of the angiogenic switch is not known, however, growth factors and signal transduction are expected to be key components in the investigation of angiogenic regulatory mechanisms.

Historically, the first angiogenesis factor isolated was basic fibroblast growth factor (bFGF). Others include vascular endothelial growth factor (VEGF), interleukin-8, hepatocyte growth factor, platelet derived endothelial growth factor (PD-ECGF), and corticotropin-releasing hormone (CRH). The discovery of endogenous angiogenesis simulators naturally led researchers to ask whether there existed endogenous angiogenesis inhibitors. Interferon-alpha, which inhibits the replication of primary endothelial cells, was the first endogenous angiogenesis inhibitor discovered. Other naturally occurring small molecules which have been discovered to have anti-angiogenic activity include the retinoids and curcumin, a small molecular weight compound which is isolated from the commonly used spice turmeric. Recently, a number of chalcone analogs have been synthesized and have been shown to exhibit activity as anti-angiogenic agents.

Among the angiogenisis inhibitors, retinoids (vitamin A and its derivatives) play an important role in the development and differentiation of epidermal cells, as well as in reversing precancerous lesions. A number of references disclose retinoids being used in cancer prophylaxis and as inducers of cell differentiation. Kizaki et al., *Seminars in Oncology* 19(1):95-105 (1992), for example, report that retinoids are potential anti-carcinogenic agents in many experimental models and that they inhibit growth and induce differentiation in transformed neoplastic cells.

The solenopsins are piperidine alkaloids which are derived from the venom of the red fire ant *Solenopsis invicta*. The venom of this insect consists of 95% alkaloids and the remainder contains solubilized proteins, amino acids and enzymes including hyaluronidase and phospholipase. Among the piperidine alkaloids, the two major components are Solenopsin A, a trans-2-methyl 6-n-undecylpiperidine and Solenopsin B, a 2,6-trans-dialkyl-piperidine.

Recently, a number of novel solenopsin analogs have been synthesized and presented as inhibitors and/or suppressants of fire ants and other insects. Another use of the solenopsins is for the elimination of ticks, fleas or other parasitic infections in dogs and cats as disclosed by Rehmert, et al. in U.S. Pat. Nos. 4,910,209, 5,075,320, and 5,098,914. In this approach, the solenopsins are administered as the whole body extract of the insect or from an oral dosage form containing more highly purified material. The administration of these drugs over a period of one to eleven days with regular booster dosages disseminates the alkaloid composition through the blood and tissue fluids of the treated animals and eliminates fluid-feeding parasites.

In the whole body version, the insects are ground to a fine texture, inserted into soluble capsules as whole body extract along with an edible carrier material such as fish oil, and are kept frozen until administration. The venom is kept refrigerated in order to maintain its effectiveness. Additionally, each insect is considered to contain approximately one venom unit or 40 nanoliters of the solenopsins, Solenopsin A and Solenopsin B.

Typically, 100-400 units of such extracts are given consecutively to dogs weighing four to 120 pounds over 11 days. However, day two is skipped to allow the animal to react to the dosage. Complete elimination of tick and flea infestation was achieved. Similarly, 100-200 units were administered in cats as well and resulted in same results. Booster doses are also given monthly in order to prevent re-infestation of such parasites.

Synthetically produced Solenopsin A is effective as well and results in complete elimination of blood and tissue- and fluid-feeding parasites. Unlike the whole body extract, it does not require refrigeration. However, higher number of units of the synthetic version are required for effective treatment. For example, 1500 units of synthetically produced Solenopsin A are equivalent to 250 units of the whole body extracts. As much as 6000 units of Solenopsin A has been used over a shorter time period and did not cause any ill effects.

Oral dosage capsules in the range of 1500 units are typically prepared by mixing 50-60 microliters of Solenopsin A with 0.1 ml of isopropylalcohol, 20 mg of fumed silica and 150 mg of microcrystalline cellulose as a carrier material. They are then packaged into soluble capsules.

The solenopsins have demonstrated low toxicity and also have shown to be more effective than the organophosphates whose efficacy has decreased due to the development of resistance in parasites. Furthermore, they are also excellent alternatives to the organophosphates which are toxic to cats.

OBJECTS OF THE INVENTION

It is an object of the invention to provide pharmaceutical compositions which exhibit activity as inhibitors of angiogenesis.

It is another object of the invention to provide pharmaceutical compositions which can be used to treat tumors and/or cancer.

It is an additional object of the present invention to provide pharmaceutical compositions based upon solenopsin and its analogs for use in treating angiogenic skin disorders such as psoriasis, acne, venous ulcers, rosacea, warts, eczema, hemangiomas, lymphangiogenesis, among numerous others, as well as internal malignancies (e.g., colon, cervical, bladder), oral malignancies cutaneous malignancies and inflammation.

It is yet another object of the invention to provide a method of treating tumors and/or cancer as well as the above-referenced angiogenic skin disorders It is still another object of the present invention to provide compounds which exhibit anti-angiogenesis and/or anti-tumor activity and are relatively inexpensive to synthesize and formulate as pharmaceutical compositions.

It is yet another object of the present invention to enhance the inhibition of Map kinase and the phosphoinositide cascade.

Any one or more of these and/or other objects of the present invention may be readily gleaned from a description of the invention which follows.

SUMMARY OF THE INVENTION

The present invention relates to pharmaceutical compositions comprising anti-angiogenesis, anti-tumor or anti-cancer effective amounts of compounds or pharmaceutically acceptable salts, thereof of the formula:

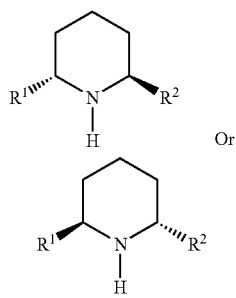

wherein $R^1$ and $R^2$ are selected from a $C_1$ to $C_{20}$, preferably a $C_1$ to $C_9$ saturated or unsaturated linear, cyclic or branch-chained substituted or unsubstituted hydrocarbon group, including a substituted or unsubstituted aromatic group. The above-mentioned hydrocarbon group may be substituted with a substituted or unsubstituted aromatic group (an example of such a group would be a benzyl group). In addition, each of $R^1$ and $R^2$ may be an ester group, preferably, a $C_1$ to $C_6$ alkyl ester group. In preferred embodiments, where $R^1$ or $R^2$ contains an unsaturated group, such as an alkenyl group, the double bond preferably is found in the alkyl chain between the carbon atom bonded to the piperidine ring and the adjacent carbon atom ($\alpha$ and $\beta$ carbons). Where either $R^1$ or $R^2$ is a saturated or unsaturated hydrocarbon group (for example, an alkyl or alkenyl group) or an ester group, the other of $R^1$ or $R^2$ is preferably a methyl group. The present compounds may be used in their neutral form, or more preferably, as their more water soluble salt forms.

In the present compounds, $R^1$ and $R^2$ are preferably straight or branch-chained alkyl or alkenyl groups, cyclic alkyl groups such as cyclopentyl or cyclohexyl groups, alkylphenyl or alkenyl phenyl groups or alkyl ester alkanoate or alkyl ester alkenoate groups.

$R^1$ and $R^2$ are more preferably selected from the group consisting of methyl, ethyl, propyl, butyl, pentyl, hexyl, heptyl, 4-methylpentyl, 5-methylhexyl, cyclopentyl, cyclohexyl, vinyl, propenyl, butenyl, pentenyl, hexenyl, heptenyl, 3-methylbutenyl, 5-methylhexenyl, benzyl, ethylbenzene, propylbenzene, ethyl propanoate and ethyl propenoate. A number of these preferred groups are depicted diagrammatically in attached FIG. 1. $R^1$ is preferably a methyl group.

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

The present invention is also directed to methods for the treatment of tumors and/or cancer, internal, cutaneous and oral malignancies, angiogenic skin disorders and inflammation, including chronic inflammatory disease comprising administering an effective amount of one or more compounds according to the present invention to a patient in need of therapy, thereof.

More particularly, the present invention relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Treatment and prevention in high risk patients of internal malignancies such as eye or ocular cancer, rectal cancer, colon cancer, cervical cancer, prostate cancer, breast cancer and bladder cancer, among numerous others, cutaneous malignancies and oral malignancies are also contemplated by the present invention.

Methods for treating angiogenic skin disorders such as psoriasis, acne, rosacea, warts, eczema, hemangiomas, lymphangiogenesis as well as inflammation such as chronic inflammatory disease, including arthritis, lupus and scleroderma are also contemplated by the present invention, such methods comprising administering a therapeutically effective amount of one or more of the disclosed compounds to a patient in need of such treatment.

BRIEF DESCRIPTION OF THE FIGURES

FIG. I is a diagrammatic representation of certain preferred compounds which are used in the pharmaceutical compositions and methods according to the present invention.

FIGS. II-IV set forth schemes for the chemical synthesis of the compounds which are used as active agents in the pharmaceutical compositions according to the present invention.

Figure 1:
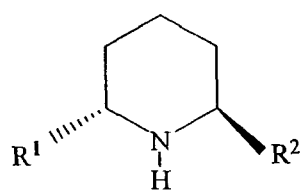
Figure 1:
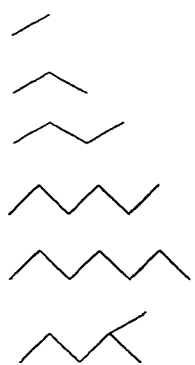
Figure 1:
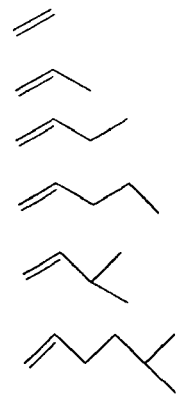
Figure 1:
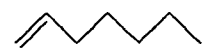
Figure 1:
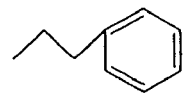
Figure 1:
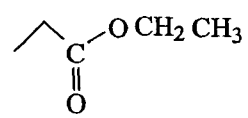
Figure 1:
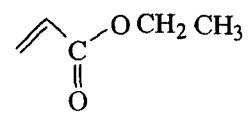
Figure 1:
Figure 1:
Figure 2:
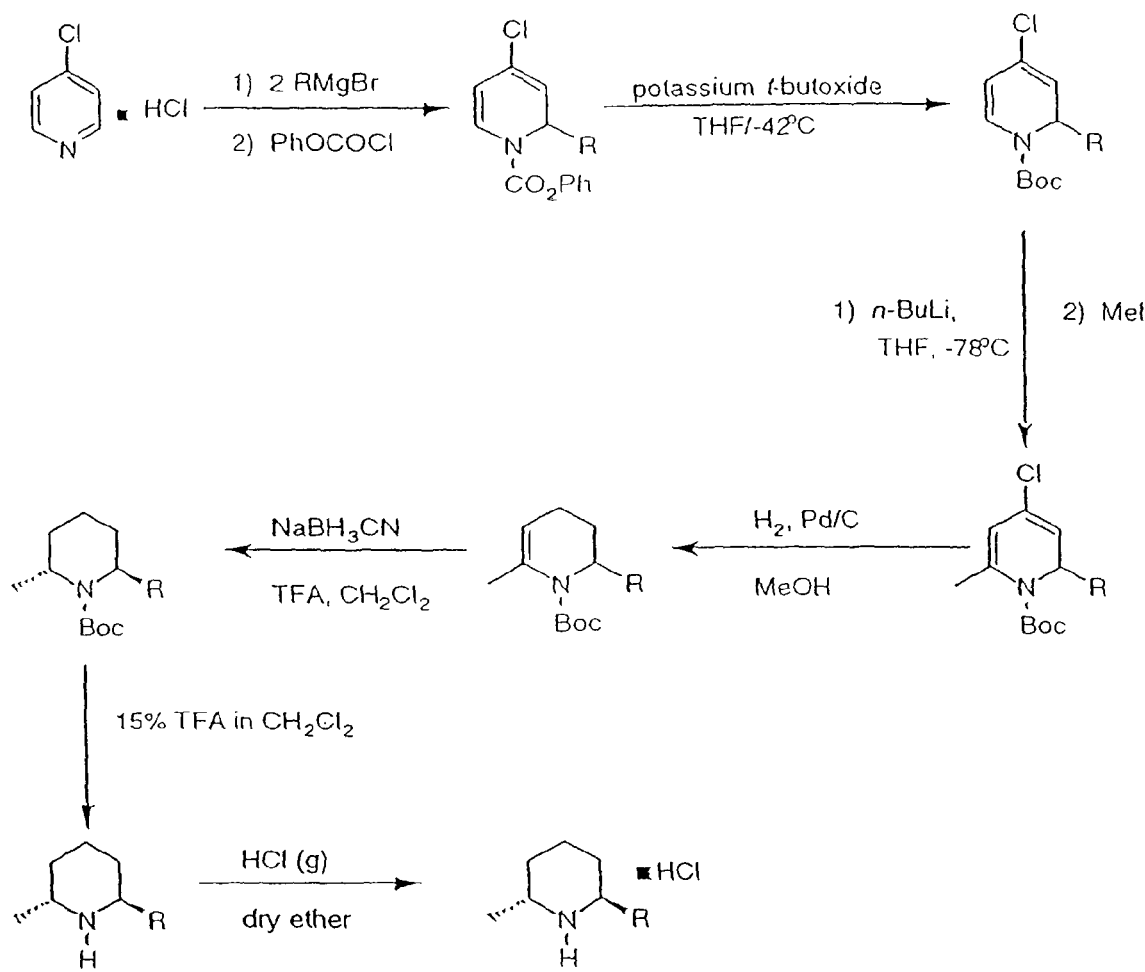
Figure 2:
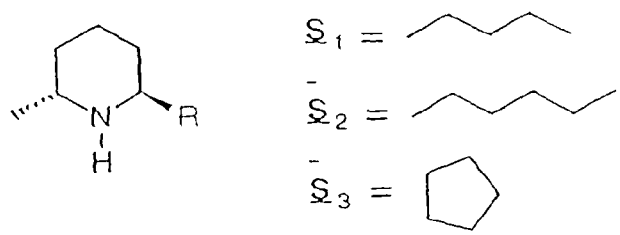
Figure 3:
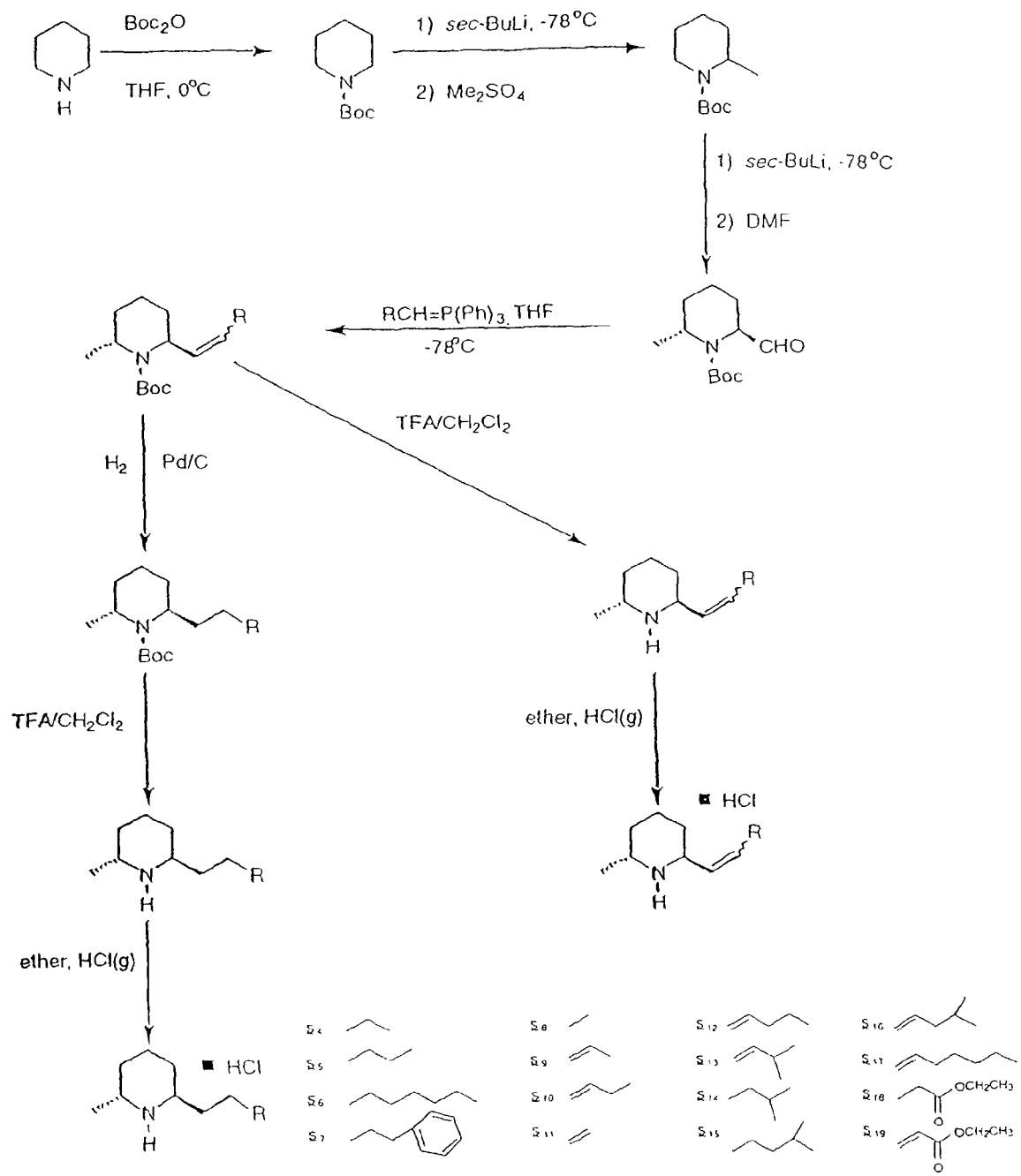
Figure 4:
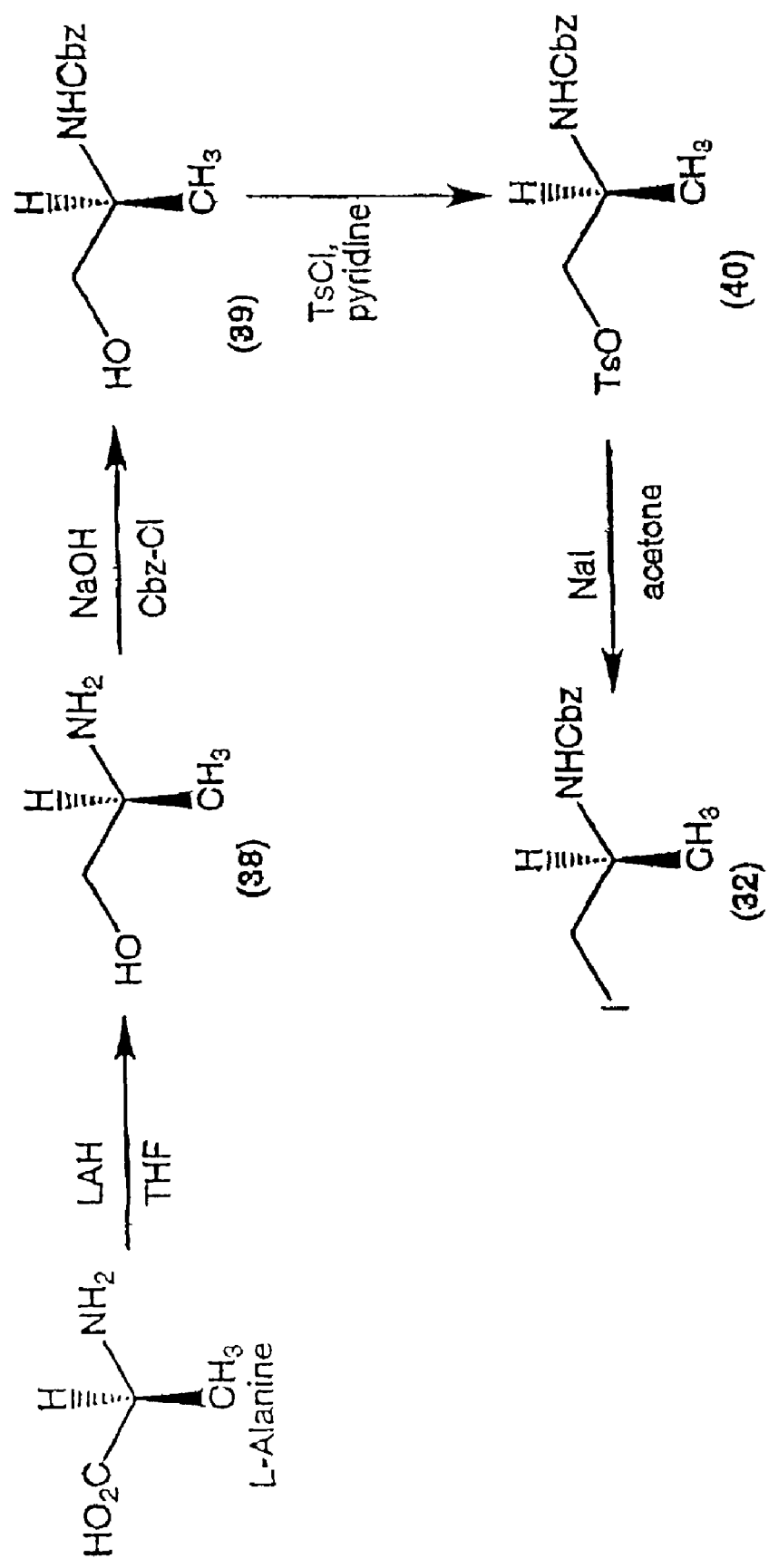

FIG. V shows the results of dose responses of Solenopsin analogs in SVR cells (reflected as % cell growth inhibition) as set forth in examples of the present application.

DETAILED DESCRIPTION OF THE INVENTION

The following terms shall be used throughout the specification to describe the present invention.

The term "patient" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

The term "effective amount" is used throughout the specification to describe concentrations or amounts of compounds or compositions according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated and the effect that inhibition of angiogenesis may have. In the present invention, pharmaceutical compositions are used to treat various disease states or conditions in mammals, preferably humans.

The term "angiogenesis" is used throughout the specification to describe the biological processes which result in the development of blood vessels or increase in the vascularity of tissue in an organism. With respect to the present invention, the term angiogenesis is defined as the process through which tumors or other rapidly proliferating tissue derive a blood supply through the generation of microvessels.

The term "tumor" is used to describe an abnormal growth in tissue which occurs when cellular proliferation is more rapid than normal tissue and continues to grow after the stimuli that initated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized. The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor.

The terms "angiogenic disease", "angiogenic disorder" and "angiogenic skin disorder" are used throughout the specification to describe a disorder, generally a skin disorder or related disorder which occurs as a consequence of or which results in increased vascularization in tissue. Oftentimes, the etiology of the angiogenic disease is unknown. However, whether angiogenesis is an actual cause of a disease state or is simply a condition of the disease state is unimportant, but the inhibition of angiogenesis in treating or reversing the disease state or condition is an important aspect of the present invention. Examples of angiogenic skin disorders which may be treated utilizing compounds according to the present invention include, for example, psoriasis, venous ulcers, acne, rosacea, warts, eczema, hemangiomas and lymphangiogenesis, among numerous others, including Sturge-Weber syndrome, neurofibromatosis, tuberous sclerosis, chronic inflammatory disease and arthritis. Any skin disorder which has as a primary or secondary characterization, increased vascularization, is considered an angiogenic skin disorder for purposes of the present invention and is amenable to treatment with compounds according to the present invention.

The term "rosacea" is used to describe acne rosacea or erythematosa characterized by vascular and follicular dilation involving the nose and contiguous portions of the cheeks. Rosacea may vary from very mild but persistent erythema to extensive hyperplasia of the sebaceous glands with deep-seated papules and pustules and accompanied by telangiectasia at the affected erythematous sites. Also called hypertrophic rosacea or rhinophyma, depending upon the severity of the condition.

The term "wart" is used to describe a small, usually hard tumerous growth on the skin. Also known as a verrucas, a wart is a flesh-colored growth of the skin which is characterized by circumscribed hypertrophy of the papillae of the corium, with thickening of the malpighian, granulation and keratin layers of the epidermis. Verucca vulgaris, a subset of warts or verruca, is characterized by infection of the keratinocytes with human papillomavirus.

The term "psoriasis" is used to describe a skin condition which is characterized by the eruption of circumscribed, discrete and confluent, reddish, silvery-scaled maculopapules; the lesions occur preeminently on the elbows, knees, scalp and trunk and microscopically show characteristic parakeratosis and elongation of rete ridges.

The term "acne" is used to describe a condition of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolescence due to an overactive sebaceous apparatus which is believed to be affected by hormonal activity.

The term "eczema" is a generic term used to describe acute or chronic inflammatory conditions of the skin, typically erythematous, edematous, papular, vesicular, and crusting; followed often by lichenification and scaling and occasionally by duskiness of the erythema and, infrequently, hyperpigmentation. Eczema is often accompanied by the sensation of itching and burning. Eczema vesicles form by intraepidermal spongiosis. Eczema is sometimes referred to colloquially as tetter, dry tetter and scaly tetter. There are numerous subcategories of eczema, all of which are treated by one or more of the compounds according to the present invention.

The term "substituted" shall mean within the context of the particular compound described, a halogen group (preferably F, Cl or Br), a $C_1$-$C_4$ alkyl group, an OH, an O($C_1$-$C_4$ alkyl) group, a —OC(O)($C_1$-$C_4$ alkyl) group or a C(O)O($C_1$-$C_4$ alkyl) group, an aryl group or an aralkyl group (such as a benzyl or phenyl group), which optionally may be substituted on the aromatic group or on the alkylene group as otherwise described above.

The compounds of the present invention are used to treat benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, cutaneous malignancies such as basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Methods of treating tumors and/or cancer according to the present invention comprise administering to a patient in need thereof an effective amount of one or compounds according to the present invention.

A method of treating angiogenic skin disorders including psoriasis, acne, rosacea, warts and eczema, among numerous others, including Sturge-Weber syndrome, and related conditions using one or more of the disclosed compositions are other inventive aspects of the present invention. In addition, the present compounds may be used to treat venous ulcers of the skin as well. These methods comprise administering an effective amount of at least one compound according to the present invention to a patient in need of treatment or therapy.

Further inventive aspects of the present invention relate to the use of the present compositions in the treatment of arthritis and chronic inflammatory diseases, including rheumatoid arthritis and osteoarthritis, among others, such as lupus and scleroderma. These methods also are directed to the administration of effective amounts of at least one compound according to the present invention to a patient in need of treatment or therapy.

Pharmaceutical compositions based upon these novel chemical compounds comprise the above-described compounds in a therapeutically effective amount for the treatment of a condition or disease such as neoplasia, including cancer, an angiogenic skin disease or an inflammatory disease or a related condition or disease optionally in combination with a pharmaceutically acceptable additive, carrier or excipient.

Certain of the compounds, in pharmaceutical dosage form, may be used as prophylactic agents for preventing a disease or condition from manifesting itself. In certain pharmaceutical dosage forms, the pro-drug form of the compounds according to the present invention may be preferred. In particular, pro-drug forms which rely on $C_1$ to $C_{20}$ ester groups or amide groups (preferably a hydroxyl, free amine or substituted nitrogen group) which may be transformed into, for example, an amide or other group may be particularly useful in this context.

The present compounds or their derivatives, including pro-drug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, magnesium, manganese and the like, among numerous others, many of which may increase the water solubility of the compounds in final pharmaceutical dosage form.

Modifications of the active compound can affect the solubility, bioavailability and rate of metabolism of the active species, thus providing control over the delivery of the active species. The term "water soluble salt form" or "salt form" is used to describe forms of compounds according to the present invention which are in their water soluble salt form. Salt forms of compounds according to the present invention include any salt which retains the desired biological effects. Nonlimiting examples of such salts are acid addition salts formed with inorganic acids such as hydrochloric acid, hydrobromic acid, sulfuric acid, phosphoric acid, nitric acid and the like, salts formed with organic acids such as acetic acid, oxalic acid, tartaric acid, succinic acid, malic acid, ascorbic acid, benzoic acid, tannic acid, pamoic acid, alginic acid, glutamic acid, naphthalenesulfonic acids, naphthalenedisulfonic acids and glacturonic acid, among numerous others. Salts may be formed by neutralizing the nitrogen on the piperidine ring with the resulting salts exhibiting substantially greater solubility or derliverability of the instant compounds. These may also affect the bioavailability and rate of metabolism or stability of the compounds according to the present invention.

Further, the modifications can affect the anti-angiogenesis activity of the compound, in some cases increasing the activity over the parent compound. This can easily be assessed by preparing the derivative and testing its activity according to known methods well within the routineer's skill in the art.

The compounds of this invention may be incorporated into formulations for all routes of administration including for example, oral, topical and parenteral including intravenous, intramuscular, eye or ocular, intraperitoneal, intrabuccal, transdermal and in suppository form as well as in gels, creams, ointments, lotions and time release implantable preparations.

Pharmaceutical compositions based upon these novel chemical compounds comprise the above-described compounds in a therapeutically effective amount for treating neoplasia, cancer and other diseases and conditions which have been described herein, including psoriasis, acne, rosacea, warts, eczema, hemangiomas, lymphangiogenesis and chronic inflammatory diseases, including arthritis, among others, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier, excipient or additive. In general, it is preferable to administer the pharmaceutical composition in orally-administrable form, but for treatment of a number of conditions, a number of other formulations may be administered via a topical, parenteral, intravenous, intramuscular, transdermal, buccal, subcutaneous, suppository or other route, including an eye or ocular route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect to the patient.

In certain pharmaceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Pharmaceutically acceptable salt forms may be the preferred chemical form of compounds according to the present invention for inclusion in pharmaceutical compositions according to the present invention.

The amount of compound included within therapeutically active formulations according to the present invention is an effective amount for treating the infection or condition in mammals. In general, a therapeutically effective amount of the present preferred compound in dosage form usually ranges from slightly less than about 0.025 mg/kg to about 2.5 g/kg, preferably about 2.5-5 mg/kg to about 100 mg/kg of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg to about 100 mg/kg. Where drug delivery is systemic rather than topical, this dosage range generally produces effective blood level concentrations of active compound or active metabolites ranging from less than about 0.04 to about 400 micrograms/cc or more of blood in the patient.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained or controlled release by standard techniques, all of which are well known in the art.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, including humans, as patients. Thus, humans and other animals, and in particular, mammals, suffering from tumors, and in particular, cancer, or other diseases as disclosed herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated). Treatment according to the present invention can also be administered in conjunction with other conventional cancer therapies, such as chemotherapy, radiation treatment and surgery, among others.

The active compound is included in the pharmaceutically acceptable additive, excipient, carrier or diluent in an amount sufficient to deliver to a patient a therapeutically effective amount for the desired indication, without causing serious toxic effects in the patient treated.

The compound is conveniently administered in any suitable unit dosage form, including but not limited to one containing from about 1 to 3000 mg, preferably about 5 to 500 mg of active compound per unit dosage form. An oral dose of 10-250 mg is usually convenient.

The concentration of active compound in the drug composition will depend on absorption, distribution, inactivation, biotransformation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, and in certain instances depending upon the desired therapy or target, antibiotics, antifungals, antinflammatories, antiviral compounds or other agents having a distinct pharmacological effect.

Solutions or suspensions used for parenteral, intradermal, subcutaneous, transdermal or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Numerous biological assays have been used and are accepted by those skilled in the art to assess the anti-tumor, anti-cancer and anti-angiogenesis activity of compounds according to the present invention. Any of these methods can be used to evaluate the activity of the compounds disclosed herein for use in the treatment of cancer and other diseases, disease states or conditions where angiogenesis is a factor.

One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

In the case of testing the anti-angiogenic/anti-cancer activity of compounds according to the present invention, an assay based on SVR cells may be employed. See, for example, Arbiser, et al., J. Am. Acad. Derm., pp. 925-929 (June, 1999). In this assay, SVR cells, which are derived from primary murine endothelial cellsa by the sequential introduction of SV40 large T antigen and activated H-ras according to the method of Arbiser, et al., Proc. Natl. Acad. Sci. USA 1997, 94:861-6, are seeded onto a 24 well dish and treated with a compound according to the present invention at known concentration. The cell numbers are counted and compared against controls. Percent inhibition is readily determined from the data obtained. Other methods, well-known in the art, may also be used.

Chemical Synthesis

The present compounds for use in pharmaceutical dosage form are synthesized using general methods which are well known in the art. An efficient flexible chemistry may be used to synthesize Solenopsin A and analogues from Solenopsin A. The method reported by D. Comins may be used and adapted for a number of analogues according to the present invention. Comins, D. L.; Weglarz, M. A. J. Org. Chem. 1991, 56, 2506.

The Comins methodology for synthesis of solenopsin A and its analogues is set forth diagrammatically in FIG. II, Scheme I. In this method, 4-chloropyridine undergoes introduction of an R group at the 2-position of the pyridine ring using alkylmagnesium bromide in THF at −78° C. followed by treatment with phenylchloroformate to provide the respective dihydropyridine derivative. Thye dihydropyridine derivative is then converted into the corresponding N-Boc (Boc is a tertiary butyl carbonate group) derivative using potassium t-butoxide in tetrahydrofuran and −42° C. A methyl (or other alkyl group) is introduced into the 6 positoin of the dihydropyridine ring as indicated by utilizing a first step of n-BuLi in THF at −78° C. followed by introduction of the methyl (alkyl) group at the 6 position of the dihydropyridine compound utilizing methyliodide to form the dialkyl substituted chlorine substituted dihydropyridine derivative as indicated. The dialkyl substituted chorine substituted dihydropyridine derivative is then subjected to a hydrogenation procedure (hydrogen, palladium/carbon catalyst in methanol) to remove the chlorine group at the 4 position as indicated, which derivative is further hydrogenated using $NABH_3/TFA$ in methylene chloride to provide the dialkyl substituted N-boc piperidine derivative. The boc group may be readily removed using 15% trifluoracetic acid in methylene chloride to afford the dialkyl substituted piperidine derivative. Salt formation may readily occur as indicated using the appropriate acid to acidify the basic nitrogen.

In an alternative chemical synthetic method, a more efficient route to the dialkyl substituted piperidine analogues according to the present invention is used. This route also allows the facile introduction of a double bond in the side chain of the 2 position of the piperidine ring. The method follows the chemical methods which are reported by Beak, et al. See Beak, P.; Lee, W. K. J. Org. Chem. 1993, 58, 1109 and Tetrahedron Lett. 1989, 30, 1197. This method demonstrated a regioselective and diastereoselective method for a lithiation-substitution at a methylene group.

As set forth in FIG. III, Scheme II, N-boc piperidine is subjected to sec-Bull at −78° C. followed by dimethylsulfate to provide the methyl substituted N-Boc piperidine analog. The N-Boc piperidine analog prepared above is then subjected to sec-BuLi at −78° C. followed by dimethyl formamide to produce the formyl piperidine derivative which can be further reacted using a Wittig procedure to produce longer chain alkylated products (saturated or unsaturated, as indicated in Scheme II). If one desires an unsaturated side chain, the Wittig reaction may afford such a substituent directly, followed by removal of the Boc group using procedures. Salt formation may also readily occur, using standard methods available in the art and as otherwise described in the examples which follow.

Alternatively, to provide the alkyl (saturated) side chains, the Wittig product is reduced using hydrogen/Pd/C to provide the fully saturated side chain. The Boc group may be readily removed using the previously described method, followed by salt formation.

The above-described methods of chemical synthesis may be readily adapted by those of ordinary skill to substitute different side chains at the 2 and 6 position of the piperidine ring to produce the compounds according to the present invention. These methods may be readily adapted to produce a large number of side chains according to the present invention.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Experimental Data

General Procedures. Analytical thin-layer chromatography (TLC) was performed on Whatman silica gel plates with a UV indicator. Visualization was accomplished by PMA, vanillin, or UV light (254 nm). All reactions were run under an atmosphere of nitrogen and monitored by TLC analysis until the starting material was completely consumed. Unless otherwise indicated, all ethereal workups consisted of the following procedure: the reaction was quenched at room temperature with water. The organic solvent was removed under reduced pressure on a rotary evaporator and the residue was taken up in ether, washed with brine and dried over anhydrous $NaSO_4$. Filtration, followed by concentration under reduced pressure on a rotary evaporator afforded a crude residue which was purified by flash chromatography using silica gel 60 (230-400 mesh) and reagent grade solvents (hexanes, ethyl acetate, ether). Microanalysis was performed by Atlantic Microlab, Inc., Atlanta, Ga. All spectra were obtained in $CDCl_3$. Proton NMR spectra were calibrated using trace $CHCl_3$ as an internal reference.

Chemical synthesis was performed as set forth in detail hereinbelow. The following abbreviations are used in the description of the chemical synthesis.

$Ac_2O$ . . . acetic anhydride
$Boc_2O$ . . . di-tert-butyl dicarbonate
Cbz-Cl . . . benzyl chloroformate
DMF . . . N,N'-dimethylformamide
EtOAc . . . ethyl acetate
LAH . . . lithium aluminum hydride
LDA . . . lithium diisopropylamide
MsCl . . . methanesulfonyl chloride
NMP . . . N-methyl-2-pyrrolidone
TBS-Cl . . . tert-butyl-dimethylchlorosilane
t-BuOK . . . potassium tert-butoxide
TEA . . . triethylamine
TFA . . . trifluoroacetic acid
THF . . . tetrahydrofuran
THP . . . tetrahydropyran
TMEDA . . . N,N,N',N'-tetramethylethylenediamine
TsCl . . . para-toluenesulfonyl chloride
TsOH . . . para-toluenesulfonic acid LAH Reduction of L-Alanine to give the corresponding alcohol (38, FIG. IV). Lithium aluminum hydride (12.78 g, 336.7 mmol) was suspended in anhydrous THF (550 mL) at 0° C. To this mixture was added L-alanine (15.0 g, 168.4 mmol) in portions over a 20 min period. The mixture was then refluxed for 10 h. To the cooled reaction mixture (0° C.) was added 2.0 M NaOH (70 mL). After stirring at room temperature for 3 h, the mixture was filtered and the solids were washed with THF (200 mL). The solids were suspeneded in THF (250 mL), and the resulting mixture was refluxed for 1 h. The solution was filtered and the solids were washed with THF (100 mL). This procedure was repeated twice. The crude alcohol was never isolated, and was used immediately in the next step.

Cbz protection of the crude alcohol to give the corresponding N-Cbz protected derivative (39). To the combined THF solutions obtained in the previous procedure was added 2.0 M NaOH (168 mL) and benzyl chlorformate (30.2 g, 176.8 mmol). After stirring for 1 h, the biphasic system was separated and the aqueous phase extracted with ethyl acetate (50 mL). The combined organic extracts were dried with $MgSO_4$, filtered and the solvent removed by evaporation to give the N-crude alcohol. This material was purified by recrystallization from THF/cyclohexane to afford the pure alcohol as white needles. mp 79.2-82.7° C. $^1H$ NMR (250 MHz) δ 7.34-7.21 (m, 5H), 5.22-5.19 (br s, 1H), 5.05 (s, 2H), 3.79-3.74 (m, 1H), 3.57-3.53 (m, 1H), 3.48-3.45 (m, 1H), 3.10-3.08 (br s, 1H), 1.12-1.09 (d, 3H); FT-IR (neat) 3453, 3036, 1715, 1517, 1458, 1330, 1266, 1242, 1092, 1032, 696 $cm^{-1}$; MS, m/z 191, 178, 134, 108, 107, 91, 79, 51, 44, 42, 31, 27.

Formation of Tosylate (40). To a stirred solution of compound obtained above, (10.0 g, 47.79 mmol) in 15 mL of pyridine at 0° C. was added p-toluenesulfonyl chloride (9.38, 49.22 mmol). The mixture was allowed to warm to room temperature. After stirring 12 h, ether (50 ml) was added, and the mixture was filtered followed by washing of the solids with additional ether. The combined organic extracts were washed with 0.5N $H_2SO_4$ (3×20 mL), 5% aqueous $NaHCO_3$ (20 mL), saturated brine, and dried with $MgSO_4$. Evaporation of the solvent in vacuo afforded the crude tosylate (13.10 g, 75%). Recrystallization was accomplished with THF/hexanes to give the product as white needles. mp 66.2-69.0° C. $^1H$ NMR (250 MHz) δ 7.76-7.74 (d, 2H), 7.34-7.27 (m, 7H), 5.07-4.99 (m, 2H), 4.86-4.84 (br s, 1H), 4.01-3.95 (m, 3H), 2.40 (s, 3H), 1.12-1.16 (d, 2H); FT-IR (neat) 3453, 3026, 1722, 1512, 1456, 1358, 1262, 1209, 1180, 976, 830, 697, 662 $cm^{-1}$. MS, m/z 363, 262, 178, 156, 134, 108, 91, 79, 65, 39, 28.

Displacement of Tosylate to give Iodocarbamate (32). To a stirred solution of the tosylate obtained above (9.61 g, 26.4 mmol) in 100 mL of acetone at 0° C. was added solid NaI (37.0 g, 264 mmol). After 30 min, the reaction was allowed to warm to room temperature and stirring was continued for 48 h. The solvent was then removed by evaporation. The resulting orange solid was suspended in ethyl acetate (150 mL). This mixture was filtered, and the solids were washed with additional ethyl acetate (100 mL). The organic solution was washed with water, 5% $Na_2S_2O_3$, and saturated brine. The resulting clear solution was dried with $Na_2SO_4$. Filtration and removal of the solvent by evaporation gave the crude iodide (iodocaramate). The material was purified by recrystallization from THF/hexanes to afford the pure product (80%) as white needles. mp 75.8-77.5° C. $^1$H NMR (250 MHz) δ 7.38-7.32 (m, 5H), 5.09-5.06 (m, 1H), 4.84-4.82 (br s, 1H), 3.59-2.55 (m, 1H), 3.41-3.39 (m, 1H), 3.29-3.26 (m, 1H), 1.24-1.22 (d, 3H); FT-IR (neat) 3451, 3038, 2980, 1727, 1553, 1513, 1455, 1404, 1327, 1231, 1211, 1100, 1019, 953, 657 cm$^{-1}$. MS, m/z 319, 169, 127, 108, 92, 79, 65, 50, 41, 28.

4-Chloro-1-(phenoxycarbonyl)-2-n-undecyl-1,2-dihydropyridine. To a stirred mixture of magnesium turnings (0.584, 24 mmol) in 40 ml of anhydrous diethyl ether was added 1-bromoundecane (5.36 mL, 24 mmol). After a self sustained reflux period of 10 minutes, the solution was refluxed an additional 45 min and then allowed to cool to room temperature. The newly formed Grignard was canulated in a stirred solution of 4-chloropyridine hydrochloride (1.5 g, 10 mmol) in 80 ml of THF at −78° C. After 20 minutes, phenyl chloroformate (1.26 ml, 10 mmol) was added dropwise. Stirring was continued for 30 min. longer at −78° C. The cooling bath was removed and the reaction mixture was allowed to stir for 30 minutes longer while slowly warming to room temperature. 20% NH$_4$Cl (30 ml) and ether (40 ml) were added and the layers separated, and the aqueous layer was extracted with two 25 ml portions of ether. The combined organic extracts were washed successively with 25 ml portions of saturated CuSO$_4$, water, saturated NaHCO$_3$, and brine. The organic phase was dried with MgSO$_4$, the solvent was evaporated, to yield the crude product as a yellow oil. Purification by column chromatography with 5% EtOAc in hexanes afforded 3.4 g (88%) of the product as a clear oil which was homogeneous by TLC analysis. $^1$H NMR (300 MHz) 67.45-7.10 (m, 5H), 6.94-6.86 (pair of d, 1H), 5.68 (d, 1H), 5.41-5.29 (dd, 1H), 5.02-4.85 (m, 1H), 1.83-1.40 (m, 2H), 1.24 (br s, 18H), 0.88 (t, 3H); FT-IR (neat) 2954, 2923, 2852, 1735, 1635, 1592, 1495, 1471, 1332, 1202, 1050 cm$^{-1}$.

1-(tert-Butoxycarbonyl)-4-chloro-2-n-undecyl-1,2-dihydropyridine. To a stirred solution of the 4-Chloro-1-(phenoxycarbonyl)-2-n-undecyl-1,2-dihydropyridine (5.31 g, 13.62 mmol) in 157 ml of THF at −42° C. was added dropwise over 15 minutes a 11.0M solution of potassium t-butoxide (54.5 ml, 54.5 mmol). The resulting orange solution was stirred for 1 h at −42° C. The cooling bath was removed, and the reaction mixture was allowed to stir for 20 min while being slowly warmed to room temperature. Water (40 ml) and ether (80 ml) were added and the aqueous phase was extracted twice with ether. The combined organic extracts were washed with cold 1.0 N NaOH (2×35 ml), and brine. The organic phase was dried over MgSO$_4$, filtered through Celite, and concentrated by evaporation to give the crude product. Column chromatography with 5% EtOAc in hexanes afforded 3.5 g (83%) of the product as a colorless oil which was homogeneous by TLC analysis. $^1$H NMR (300 MHz) d 6.92-6.61 (pair of br d, 1H), 5.53 (pair of br d, 1H), 5.55 (br s, 1H), 5.25-5.11 (pair of br d, 1H), 4.82-4.63 (br m, 1H), 1.53 (s, 9H), 1.24 (br s, 20H), 0.83 (t, 3H); $^{13}$C NMR (75 MHz) 152.6 (s), 151.8 (s), 127.7 (s), 127.5 (s), 117.8 (s), 117.4 (s), 106.6 (s), 106.2 (s), 81.7 (s), 54.1 (s), 53.2 (s), 34.3 (s), 33.8 (s), 31.9 (s), 29.7 (s), 29.6 (s), 29.5 (s), 29.3 (s), 28.1 (s), 24.3 (s), 22.7 (s), 14.1 (s) ppm; FT-IR 2954, 2926, 2855, 1717, 1633, 1369, 1390, 1171, 1145, 1129, 1054 cm$^{-1}$.

1-(tert-Butoxycarbonyl)-4-chloro-6-methyl-2-n-undecyl-1,2-dihydropyridine. To a stirred solution of 1-(tert-Butoxycarbonyl)-4-chloro-2-n-undecyl-1,2-dihydropyridine (3.15, 8.51 mmol) in 115 ml of THF at −42° C. was added n-butyllithium (6.4 mL, 10.2 mmol, 1.6 M solution in hexanes) dropwise via syringe. After the mixture had stirred at −42° C. for 1 h, iodomethane (1.6 mL, 25.54 mmol) was added and stirring was continued at −42° C. for 1 h and then at room temperature for 1 h. Water (30 mL) and ether (60 mL) were added, the layers were separated, the aqueous phase was extracted with ether (2×15 mL), and the combined organic extracts were washed with brine. The organic phase was dried over K$_2$CO$_3$ filtered through silica gel/Celite, and concentrated in vacuo to give the crude product. Purification by column chromatography gave with 5% EtOAc in hexanes afforded 2.5 g (77%) of the product as a clear orange oil which was homogeneous by TLC analysis. $^1$H NMR (250 MHz) d 5.62 (dd, 1H), 5.30 (m, 1H), 4.76 (dt 1H), 2.16 (s, 3H), 1.53 (s, 9H), 1.48-1.40 (m, 2H), 1.26 (br s, 18H), 0.84 (t, 3H); $^{13}$C NMR (62.7 MHz) 153.1 (s), 137.1 (s), 126.6 (s), 119.4 (s), 112.3 (s), 81.4 (s), 54.2 (s), 31.9 (s), 31.8 (s), 29.69 (s), 29.63 (s), 29.55 (s), 29.44 (s), 29.36 (s), 29.33 (s), 28.2 (s), 24.6 (s), 22.7 (s), 22.0 (s), 14.1 (s) ppm. FT-IR (neat) 2956, 2924, 2852, 1709, 1637, 1471, 1393, 1368, 1342, 1169, 1131 cm$^{-1}$.

1-(tert-Butoxycarbonyl)-6-methyl-2-n-undecyl-1,2,3,4-tetrahydropyridine. To a stirred solution of 2.17 g, (5.65 mmol) of 1-(tert-Butoxycarbonyl)-4-chloro-6-methyl-2-n-undecyl-1,2-dihydropyridine in 120 mL of MeOH at 0° C. was added 0.422 g (5.71 mmol) of lithium carbonate followed by of 5% Pd/C. The flask was evacuated and filled with hydrogen repeatedly. The system was placed under positive pressure from a balloon, and the reaction was monitored by removing aliquots with a syringe, concentrating the aliquot in vacuo, and examing its $^1$H NMR spectrum. Upon completion, the mixture was filtered through Celite, and concentrated by evaporation. The residue was dissolved in ether (20 mL), water (20 mL) was added, and the aqueous phase was extracted twice with ether (2×10 mL). The combined organic extracts were washed with 1M NaOH (2×20 ml) and brine. The organic products were dried over K$_2$CO$_3$, filtered through Celite, and concentrated in vacuo to give the crude product. Purification by column chromatography, (silica gel, 10% ether in hexanes) afforded 1.35 g (70%) the product as a light yellow oil which was homogeneous by TLC analysis. $^1$H NMR (300 MHz) δ 4.75 (br s, 1H), 4.62 (m, 1H), 2.21 (s, 3H), 1.91-1.64 (m, 4H), 1.52 (s, 9H), 1.28 (br s, 20H), 0.90 (t, 3H); $^{13}$C NMR (75 MHz) 154.1 (s), 133.5 (s), 110.4 (s), 79.6 (s), 52.1 (s), 32.3 (s), 30.1 (s), 30.0 (s), 29.9 (s), 28.5 (s), 26.7 (s), 23.5 (s), 23.2 (s), 19.8 (s), 14.4 (s) ppm. FT-IR (neat) 2928, 2860, 1694, 1457, 1368, 1352, 1168, 1124, 1095, 1073 cm$^{-1}$.

trans-N-Boc-2-methyl-6-n-undecylpiperidine. To a stirred solution of 1.34 g (3.81 mmol) of 1-(tert-Butoxycarbonyl)-6-methyl-2-n-undecyl-1,2,3,4-tetrahydropyridine in 260 mL of CH$_2$Cl$_2$ was added 1.44 g (22.86 mmol) of sodium cyanoborohydride. After being stirred 15 minutes at room temperature, the heterogeneous solution was cooled to −42° C. and TFA (3.7 mL, 38.10 mmol) was added slowly dropwise. After being stirred for 4 h at −42° C., the cold bath was removed, and the reaction mixture was immediately quenched with 190 mL of a saturated aqueous NaHCO$_3$/THF mixture (50:50). The aqueous phase was extracted with CH$_2$Cl$_2$ (2×40 mL) and the combined organic extracts were washed with water and brine. The organic phase was dried with K$_2$CO$_3$, filtered through Celite, and evaporated to give the crude product. Column chromatography using 5% EtOAc in hexanes gave 0.9 g (67%) of the product as a clear colorless oil. $^1$H NMR (300 MHz) d 3.97-3.84 (m, 1H), 3.83-3.74 (m, 1H), 1.92-1.28 (m, 8H), 1.46 (s, 9H), 1.25 (br s, 18H), 1.22 (d, 3H), 0.89 (t, 3H); $^{13}$C NMR (75 MHz) 155.3 (s), 78.7 (s), 51.6 (s), 46.9 (s), 34.3 (s), 31.7 (s), 29.6 (s), 29.5 (s), 29.3 (s), 28.4 (s), 27.2 (s), 26.8 (s), 23.2 (s), 22.7 (s), 20.8 (s), 14.0 (s), 13.6 (s) ppm. FT-IR (neat) 2924, 2854, 2691, 1468, 1394, 1368, 1178, 1091 cm$^{-1}$.

(±)-Solenopsin A*HCl. trans-2-methyl-6-n-undecylpiperidine hydrochloride. To a stirred solution of 0.463 g of trans-N-Boc-2-methyl-6-n-undecylpiperidine in 50 ml of $CH_2Cl_2$ at 0° C. was added dropwise 12.2 mL (excess) of trifluoroacetic acid. The cooling bath was removed, and stirring was continued for 1 h at room temperature. After concentrating the resulting solution on a rotary evaporator, the remaining liquid was dissolved in ether (50 mL), and 25 ml of water was added. The aqueous phase was extracted with ether (2*40 mL), and the combined organic extracts were washed with saturated $NaHCO_3$ (2*40 mL) and brine. The organic phase was dried over $K_2CO_3$, filtered through Celite, and concentrated in vacuo to give an oil. The crude product was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as white needles. $^1$H NMR (300 MHz) δ 9.30 (br s, 2H), 3.53 (br s, 1H), 3.27 (br s, 1H), 1.96-1.22 (m, 29H), 0.85 (t, 3H); $^{13}$C NMR (75 MHz) 52.0 (s), 48.2 (s), 32.1 (s), 31.0 (s), 29.8 (s), 29.75 (s), 29.7 (s), 29.6 (s), 29.5 (s), 29.2 (s), 26.5 (s), 26.1 (s), 22.9 (s), 17.6 (s), 17.1 (s), 14.3 (s) ppm. FT-IR (neat) 3420, 2931, 2853, 1465, 1376, 1141, 1067 $cm^{-1}$.

4-Chloro-1-(phenoxycarbonyl)-2-n-pentyl-1,2-dihydropyridine. To a stirred mixture of 4-chloropyridine hydrochloride (3 g, 20 mmol) in 200 mL of THF at −78° C. was added 24 mL (48 mmol) of pentylmagnesium bromide (2M soln in ether) slowly dropwise. After being stirred at −78° C. for 20 minutes, phenyl chloroformate (2.51 mL, 20 mmol) was added and the mixture was stirred for 30 minutes at −78° C. The cooling bath was removed and the reaction mixture was allowed to stir while slowly warming to room temperature. Aqueous 20% $NH_4Cl$ (50 mL) and ether (80 mL) were added, the layers were separated, and the queous phase was extracted twice with ether. The combined organic extracts were washed successively with 50 mL portions of saturated aqueous $CuSO_4$, water, saturated $NaHCO_3$, and brine. The organic phase was dried over $MgSO_4$, filtered through Celite, and evaporated to give 6.2 g (quantitative) of the crude product. This crude material was used directly in the next step to make the N-Boc derivative. $^1$H NMR (250 MHz) d 7.45-7.05 (m, 5H), 5.68 (d, 1H), 5.33 (m, 1H), 4.92 (m, 1H), 1.9-1.1 (m, 8H), 0.87 (t, 3H).

1-(tert-Butoxycarbonyl)-4-chloro-2-n-pentyl-1,2-dihydropyridine. To a stirred solution of 4-Chloro-1-(phenoxycarbonyl)-2-n-pentyl-1,2-dihydropyridine (7.1 g, 23.22 mmol) in 250 ml of THF at −42° C. was added dropwise over 15 minutes a 1.0M solution of potassium t-butoxide (93 mL, 92.87 mmol). The resulting orange solution was stirred for 1 h at −42° C. The cooling bath was removed, and the reaction mixture was allowed to stir for 20 min while being slowly warmed to room temperature. Water (50 ml) and ether (70 ml) were added and the aqueous phase was extracted twice with ether. The combined organic extracts were washed with cold 1.0 N NaOH (2×35 ml), and brine. The organic phase was dried over $MgSO_4$, filtered through Celite, and concentrated in vacuo to give the crude product. Column chromatography with 5% EtOAc in hexanes afforded 4.78 (73%) of the product. $^1$H NMR (250 MHz) d 6.85-6.70 (dd, 1H), 5.54 (br s, 1H), 5.19-4.91 (m, 1H), 4.72-4.51 (m, 1H), 1.69-1.26 (m, 17H), 0.89-0.84 (t, 3H); $^{13}$C NMR (62.7 MHz) 151.8 (s), 127.5-126.6 (d), 117.8-117.4 (d), 106.6-106.1 (d), 81.7 (s), 54.0 (s), 53.1 (s), 34.1 (s), 33.6 (s), 31.6 (s), 28.1 (s), 23.9 (s), 22.6 (s), 14.0 (s) ppm.

1-(tert-Butoxycarbonyl)-4-chloro-6-methyl-2-n-pentyl-1, 2-dihydropyridine. To a stirred solution of 1-(tert-Butoxycarbonyl)-4-chloro-2-n-pentyl-1,2-dihydropyridine (4.67 g, 16.33 mmol) in 170 ml of THF at −42° C. was added n-butyllithium (7.84 mL, 19.61 mmol) dropwise via syringe. After the mixture had stirred at −42° C. for 1 h, iodomethane (3.1 mL, 48.99 mmol) was added and stirring was continued at −42° C. for 1 h and then at room temperature for 1 h. Water (50 mL) and ether (100 mL) were added, the layers were separated, the aqueous phase was extracted with ether (2×15 mL), and the combined organic extracts were washed with brine. The organic phase was dried over $K_2CO_3$ filtered through silica gel/Celite, and concentrated in vacuo to give the crude product. Purification by column chromatography with 5% EtOAc in hexanes afforded 3.6 g (74%) of the product. $^1$H NMR (250 MHz) d 5.62-5.59 (d, 1H), 5.31 (br s, 1H), 4.80-4.72 (q, 1H), 2.13 (s, 1H), 1.55-1.26 (m, 17H), 0.89-0.84 (t, 3H); $^{13}$C NMR (62.7 MHz) 153.0 (s), 136.9 (s), 126.5 (s), 119.3 (s), 112.2 (s), 81.4 (s), 54.1 (s), 31.6 (s), 31.5 (s), 28.1 (s), 24.2 (s), 22.4 (s), 21.9 (s), 13.9 (s) ppm. FT-IR (neat) 2927, 2855, 1706, 1634, 1391, 1128, 1087 $cm^{-1}$.

1-(tert-Butoxycarbonyl)-6-methyl-2-n-pentyl-1,2,3,4-tetrahydropyridine. To a stirred solution of 1-(tert-Butoxycarbonyl)-4-chloro-6-methyl-2-n-pentyl-1,2-dihydropyridine (3.48 g, 11.61 mmol) in 220 mL of MeOH at 0° C. was added of lithium carbonate 0.857 g, 11.61 mmol) followed by 5% Pd/C. The mixture was placed under a positive pressure of hydrogen gas from a balloon, and the reaction progress was monitored by removing aliquots with a syringe, concentrating the aliquot in vacuo, and examining its $^1$H NMR spectrum. Upon completion, the mixture was filtered through Celite and evaporated. The residue was dissolved in ether (100 mL) and water (50 mL) was added, and the aqueous phase was extracted twice with ether. The combined organic extracts were washed with 1M NaOH and brine. The organic phase was dried with potassium carbonate, filtered through Celite, and concentrated in vacuo to give the crude product. Purification by column chromatography (silica gel, 5% EtOAc in hexanes) afforded 3.04 g (98%) of the product which was homogeneous by TLC analysis. $^1$H NMR (300 MHz) d 4.86 (br s, 1H), 4.39-4.31 (m, 1H), 2.02 (s, 3H), 1.98-1.92 (m, 2H), 1.91-1.28 (m, 21H), 0.9-0.85 (t, 3H); $^{13}$C NMR (75 MHz) 153.8 (s), 132.5 (s), 110.9 (s), 79.9 (s), 51.9 (s), 31.7 (s), 29.4 (s), 28.3 (s), 26.0 (s), 25.8 (s), 23.1 (s), 22.6 (s), 19.5 (s), 13.9 (s) ppm. FT-IR (neat) 2956, 2927, 2856, 1693, 1658, 1454, 1349, 1253, 1169, 1124, 1072 $cm^{-1}$.

trans-N-Boc-2-methyl-6-n-pentylpiperidine. To a stirred solution of 1-(tert-Butoxycarbonyl)-6-methyl-2-n-pentyl-1, 2,3,4-tetrahydropyridine (1.0 g, 3.74 mmol) in 250 mL of $CH_2Cl_2$ was added sodium cyanoborohydride (1.41 g, 22.43 mmol). After being stirred 15 minutes at room temperature, the heterogeneous solution was cooled to −42° C. and TFA (2.9 mL, 37.4 mmol) was added slowly dropwise. After being stirred for 4 h at −42° C., the cold bath was removed, and the reaction mixture was immediately quenched with 200 mL of a saturated aqueous $NaHCO_3$/THF mixture (50:50). The aqueous phase was extracted with $CH_2Cl_2$ (2×70 mL) and the combined organic extracts were washed with water and brine. The organic phase was dried with $K_2CO_3$, filtered through Celite, and evaporated to give crude product. Column chromatography using 5% EtOAc in hexanes gave 0.8 g (70%) of the product which was homogeneous by TLC analysis. $^1$H NMR (300 MHz) d 3.92-3.81 (m, 1H), 3.69-3.80 (m, 1H), 1.91-1.21 (m, 26H), 0.90-0.86 (t, 3H).

trans-2-methyl-6-n-pentylpiperidine hydrochloride. To a stirred solution of trans-N-Boc-2-methyl-6-n-pentylpiperidine (0.77 g. 2.86 mmol) in 90 ml of $CH_2Cl_2$ at 0° C. was added dropwise trifluoroacetic acid (6.6 mL, 85.72 mmol). The cooling bath was removed, and stirring was continued for 1 h at room temperature. After concentrating the resulting solution on a rotary evaporator, the remaining liquid was dissolved in ether (40 mL), and 20 ml of water was added. The aqueous phase was extracted with ether (2*10 mL), and the combined organic extracts were washed with saturated NaHCO$_3$ (2*30 mL) and brine. The organic phase was dried over K$_2$CO$_3$, filtered through Celite, and concentrated on a rotary evaporator. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as white needles. mp 109.6-110.9° C.; $^1$H NMR (300 MHz) δ 9.30 (br s, 2H), 3.53 (br. s, 1H), 3.27 (br s, 1H), 1.96-1.29 (m, 17H), 0.89-0.85 (t, 3H); $^{13}$C NMR (75 MHz) 51.7 (s), 47.9 (s), 31.4 (s), 30.6 (s), 28.8 (s), 28.1 (s), 26.1 (s), 25.4 (s), 24.9 (s), 22.4 (s), 17.3 (s), 16.8 (s). FT-IR: 3421, 2932, 1589, 1458, 1392, 1378, 1357, 1102, 727. Elemental Analysis for C$_1$H$_{24}$NCl: C, 64.21%; H, 11.76%; N, 6.81%. Found: C, 64.19%; H, 11.72%; N, 6.71%.

4-Chloro-1-(phenoxycarbonyl)-2-n-hexyl-1,2-dihydropyridine. To a stirred mixture of 4-chloropyridine hydrochloride (3 g, 20 mmol) in 200 mL of THF at −78° C. was added 24 mL (48 mmol) of pentylmagnesium bromide (2M soln in ether) slowly dropwise. After being stirred at −78° C. for 20 minutes, phenyl chloroformate (2.51 mL, 20 mmol) was added and the mixture was stirred for 30 minutes at −78° C. The cooling bath was removed and the reaction mixture was allowed to stir while slowly warming to room temperature. Aqueous 20% NH$_4$Cl (50 mL) and ether (80 mL) were added, the layers were separated, and the queous phase was extracted twice with ether. The combined organic extracts were washed successively with 50 mL portions of saturated aqueous CuSO$_4$, water, saturated NaHCO$_3$, and brine. The organic phase was dried over MgSO$_4$, filtered through Celite, and evaporated to give 6.4 g (quantitative) of the crude product. This crude material was used directly in the next step to make the N-Boc derivative. $^1$H NMR (250 MHz) δ 7.52-6.99 (m, 5H), 5.63 (d, 1H), 5.24 (m, 1H), 4.95 (m, 1H), 1.93-1.16 (m, 8H), 0.87 (t, 3H).

1-(tert-Butoxycarbonyl)$_4$-chloro-2-n-hexyl-1,2-dihydropyridine. To a stirred solution of 4-Chloro-1-(phenoxycarbonyl)-2-n-hexyl-1,2-dihydropyridine (7.42 g, 23.2 mmol) in 250 ml of THF at −42° C. was added dropwise over 15 minutes a 1.0M solution of potassium t-butoxide (93 mL, 92.87 mmol). The resulting orange solution was stirred for 1 h at −42° C. The cooling bath was removed, and the reaction mixture was allowed to stir for 20 min while being slowly warmed to room temperature. Water (50 ml) and ether (70 ml) were added and the aqueous phase was extracted twice with ether. The combined organic extracts were washed with cold 1.0 N NaOH (2×35 ml), and brine. The organic phase was dried over MgSO$_4$, filtered through Celite, and concentrated in vacuo to give the crude product. Column chromatography with 5% EtOAc in hexanes afforded 5.9 g (81% from previous reaction) as a clear colorless oil that was homogeneous by TLC analysis. $^1$H NMR (250 MHz) δ 6.85-6.63 (dd, 1H), 5.55 (br s, 1H), 5.23-5.12 (m, 1H), 4.87-4.56 (m, 1H), 1.72-1.25 (m, 19H), 0.89-0.85 (t, 3H).

1-(tert-Butoxycarbonyl)-4-chloro-6-methyl-2-n-hexyl-1,2-dihydropyridine. To a stirred solution of 1-(tert-Butoxycarbonyl)-4-chloro-2-n-hexyl-1,2-dihydropyridine (4.84 g, 16.14 mmol) in 180 ml of THF at −42° C. was added n-butyllithium (19.4 mL, 19.37 mmol) dropwise via syringe. After the mixture had stirred at −42° C. for 1 h, iodomethane (3.0 mL, 48.42 mmol) was added and stirring was continued at −42° C. for 1 h and then at room temperature for 1 h. Water (50 mL) and ether (100 mL) were added, the layers were separated, the aqueous phase was extracted with ether (2×15 mL), and the combined organic extracts were washed with brine. The organic phase was dried over K$_2$CO$_3$ filtered through silica gel/Celite, and concentrated in vacuo to give the crude product. Purification by column chromatography with 5% EtOAc in hexanes afforded 4.89 g (73.4%) of the product as an orange oil that was homogeneous by TLC analysis. $^1$H NMR (250 MHz) δ 5.65-5.58 (d, 1H), 5.32 (br s, 1H), 4.84-4.72 (q, 1H), 2.13 (s, 3H), 1.75-1.21 (m, 19H), 0.91-0.85 (t, 3H).

1-(tert-Butoxycarbonyl)-6-methyl-2-n-pentyl-1,2,3,4-tetrahydropyridine. To a stirred solution of 1-(tert-Butoxycarbonyl)-4-chloro-6-methyl-2-n-hexyl-1,2-dihydropyridine (3.74 g, 11.91 mmol) in 250 mL of MeOH at 0° C. was added of lithium carbonate (0.88 g, 11.91 mmol) followed by 5% Pd/C. The mixture was placed under a positive pressure of hydrogen gas from a balloon, and the reaction progress was monitored by removing aliquots with a syringe, concentrating the aliquot in vacuo, and examining its $^1$H NMR spectrum. Upon completion, the mixture was filtered through Celite and evaporated. The residue was dissolved in ether (100 mL) and water (50 mL) was added, and the aqueous phase was extracted twice with ether. The combined organic extracts were washed with 1M NaOH and brine. The organic phase was dried with potassium carbonate, filtered through Celite, and concentrated in vacuo to give the crude product. Purification by column chromatography (silica gel, 5% EtOAc in hexanes) afforded 2.09 g (62%) as a clear oil that was homogeneous by TLC analysis. $^1$H NMR (300 MHz) δ 4.85 (br s, 1H), 4.43-4.38 (m, 1H), 2.01 (s, 3H), 1.99-1.91 (m, 2H), 1.83-1.12 (m, 23H), 0.89-0.84 (t, 3H).

trans-N-Boc-2-methyl-6-n-hexylpiperidine. To a stirred solution of 1-(tert-Butoxycarbonyl)-6-methyl-2-n-pentyl-1,2,3,4-tetrahydropyridine (1.0 g, 3.55 mmol) in 240 mL of CH$_2$Cl$_2$ was added sodium cyanoborohydride (1.34 g, 21.3 mmol). After being stirred 15 minutes at room temperature, the heterogeneous solution was cooled to −42° C. and TFA (3.5 mL, 35.53 mmol) was added slowly dropwise. After being stirred for 4 h at −42° C., the cold bath was removed, and the reaction mixture was immediately quenched with 200 mL of a saturated aqueous NaHCO$_3$/THF mixture (50:50). The aqueous phase was extracted with CH$_2$Cl$_2$ (2×70 mL) and the combined organic extracts were washed with water and brine. The organic phase was dried with K$_2$CO$_3$, filtered through Celite, and evaporated to give crude product. Column chromatography using 5% EtOAc in hexanes gave 0.54 g (54%) of the product which was homogeneous by TLC analysis. $^1$H NMR (300 MHz) δ 3.99-3.82 (m, 1H), 3.79-3.74 (m, 1H), 1.91-1.15 (m, 28H), 0.92-0.83 (t, 3H); $^{13}$C NMR (75 Mhz) 155.6 (s), 78.6 (s), 51.6 (s), 46.9 (s) 34.34 (s), 31.9 (s), 29.3 (s), 28.5 (s), 27.1 (s), 26.9 (s), 23.1 (s), 22.6 (s), 20.8 (s), 14.0 (s), 13.7 (s) ppm.

trans-2-methyl-6-n-hexylpiperidine hydrochloride. To a stirred solution of trans-N-Boc-2-methyl-6-n-hexylpiperidine (1.14 g. 4.02 mmol) in 90 ml of CH$_2$Cl$_2$ at 0° C. was added dropwise trifluoroacetic acid (6.6 mL, 85.72 mmol). The cooling bath was removed, and stirring was continued for 1 h at room temperature. After concentrating the resulting solution on a rotary evaporator, the remaining liquid was dissolved in ether (40 mL), and 20 ml of water was added. The aqueous phase was extracted with ether (2*10 mL), and the combined organic extracts were washed with saturated NaHCO$_3$ (2*30 mL) and brine. The organic phase was dried over K$_2$CO$_3$, filtered through Celite, and concentrated on a rotary evaporator. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give 0.74 g (48%) of the piperidinium hydrochloride as white needles. mp 130.7-131.8° C.; $^1$H NMR (300 MHz) δ 9.32 (s, 2H), 3.53 (s, 1H), 3.27 (s, 1H), 2.01-1.26 (m, 19H), 0.85 (t, 3H); $^{13}$C NMR (75 MHz) δ 51.7 (s), 47.9 (s), 31.6 (s), 30.7 (s), 28.92 (s), 28.84 (s), 26.11 (s), 25.72 (s), 22.48 (s), 17.29 (s), 16.83 (s), 13.97 (s). FT-IR: 3489, 2934, 1558, 1540, 1473, 1457, 1299, 1123, 1072, 977, 885, 721. Elemental Analysis for C$_{12}$H$_{26}$NCl: C, 65.58%; H, 11.92%; N, 6.37%. Found: C, 65.60%; H, 11.86%; N, 6.27%.

4-Chloro-1-(phenoxycarbonyl)-2-cyclopentyl-1,2-dihydropyridine. To a stirred mixture of 4-chloropyridine hydrochloride (3 g, 20 mmol) in 200 mL of THF at −78° C. was added 24 mL (48 mmol) of pentylmagnesium bromide (2M soln in ether) slowly dropwise. After being stirred at −78° C. for 20 minutes, phenyl chloroformate (2.51 mL, 20 mmol) was added and the mixture was stirred for 30 minutes at −78° C. The cooling bath was removed and the reaction mixture was allowed to stir while slowly warming to room temperature. Aqueous 20% NH$_4$Cl (50 mL) and ether (80 mL) were added, the layers were separated, and the queous phase was extracted twice with ether. The combined organic extracts were washed successively with 50 mL portions of saturated aqueous CuSO$_4$, water, saturated NaHCO$_3$, and brine. The organic phase was dried over MgSO$_4$, filtered through Celite, and evaporated to give the crude product. Purification by column chromatography (silica gel, 5% EtOAc in hexanes) afforded 5.25 g (86.4%) of the product as a yellow oil that was homogeneous by TLC analysis. $^1$H NMR (250 MHz) δ 7.61-5.67 (m, 5H), 5.66 (d, 1H), 5.28 (m, 1H), 5.01 (m, 1H), 2.21 (m, 1H), 1.98-1.28 (m, 8H).

1-(tert-Butoxycarbonyl)-4-chloro-2-cyclopentyl-1,2-dihydropyridine. To a stirred solution of 4-Chloro-1-(phenoxycarbonyl)-2-cyclopentyl-1,2-dihydropyridine (5.52 g, 17.3 mmol) in 200 ml of THF at −42° C. was added dropwise over 15 minutes a 1.0M solution of potassium t-butoxide (50 mL, 50 mmol). The resulting orange solution was stirred for 1 h at −42° C. The cooling bath was removed, and the reaction mixture was allowed to stir for 20 min while being slowly warmed to room temperature. Water (50 ml) and ether (70 ml) were added and the aqueous phase was extracted twice with ether. The combined organic extracts were washed with cold 1.0 N NaOH (2×35 ml), and brine. The organic phase was dried over MgSO$_4$, filtered through Celite, and concentrated in vacuo to give the crude product. Column chromatography with 5% EtOAc in hexanes afforded 3.71 g (75.7%) of the product which was homogeneous by TLC analysis. $^1$H NMR (250 MHz) δ 6.89-6.67 (dd, 1H), 5.58 (br s, 1H), 5.27-5.23 (m, 1H), 4.92-4.62 (m, 1H), 2.21 (m, 1H), 1.892-1.25 (m, 17H).

1-(tert-Butoxycarbonyl)-4-chloro-6-methyl-2-cyclopentyl-1,2-dihydropyridine. To a stirred solution of 1-(tert-Butoxycarbonyl)-4-chloro-2-cyclopentyl-1,2-dihydropyridine (3.69 g, 12.99 mmol) in 180 ml of THF at −42° C. was added n-butyllithium (6.25 mL, 15.59 mmol) dropwise via syringe. After the mixture had stirred at −42° C. for 1 h, iodomethane (2.4 mL, 38.97 mmol) was added and stirring was continued at −42° C. for 1 h and then at room temperature for 1 h. Water (50 mL) and ether (100 mL) were added, the layers were separated, the aqueous phase was extracted with ether (2×15 mL), and the combined organic extracts were washed with brine. The organic phase was dried over K$_2$CO$_3$ filtered through silica gel/Celite, and concentrated in vacuo to give the crude product. Purification by column chromatography with 5% EtOAc in hexanes afforded 2.60 g (69%) of the product as an orange oil that was homogeneous by TLC analysis. $^1$H NMR (250 MHz) δ 5.68-5.61 (d, 1H), 5.37 (br s, 1H), 4.86-4.73 (q, 1H), 2.21 (m, 1H), 2.14 (s, 3H), 1.76-1.20 (m, 17H).

1-(tert-Butoxycarbonyl)-6-methyl-2-cyclopentyl-1,2,3,4-tetrahydropyridine. To a stirred solution of 1-(tert-Butoxycarbonyl)-4-chloro-6-methyl-2-cyclopentyl-1,2-dihydropyridine (2.54 g, 8.53 mmol) in 175 mL of MeOH at 0° C. was added of lithium carbonate (0.63 g, 8.53 mmol) followed by 5% Pd/C. The mixture was placed under a positive pressure of hydrogen gas from a balloon, and the reaction progress was monitored by removing aliquots with a syringe, concentrating the aliquot in vacuo, and examining its $^1$H NMR spectrum. Upon completion, the mixture was filtered through Celite and evaporated. The residue was dissolved in ether (100 mL) and water (50 mL) was added, and the aqueous phase was extracted twice with ether. The combined organic extracts were washed with 1M NaOH and brine. The organic phase was dried with potassium carbonate, filtered through Celite, and concentrated in vacuo to give the crude product. Purification by column chromatography (silica gel, 5% EtOAc in hexanes) afforded 1.14 g (52%) as a clear oil that was homogeneous by TLC analysis. $^1$H NMR (300 MHz) δ 4.87 (br s, 1H), 4.45-4.40 (m, 1H), 2.22, (m, 1H), 2.02 (s, 3H), 1.99-1.91 (m, 2H), 1.82-1.20 (m, 21H).

trans-N-Boc-2-methyl-6-cyclopentylpiperidine. To a stirred solution 1-(tert-Butoxycarbonyl)-6-methyl-2-cyclopentyl-1,2,3,4-tetrahydropyridine (1.14 g, 4.29 mmol) in 290 mL of CH$_2$Cl$_2$ was added sodium cyanoborohydride (1.62 g, 25.8 mmol). After being stirred 15 minutes at room temperature, the heterogeneous solution was cooled to −42° C. and TFA (4.9 mL, 42.95 mmol) was added slowly dropwise. After being stirred for 4 h at −42° C., the cold bath was removed, and the reaction mixture was immediately quenched with 200 mL of a saturated aqueous NaHCO$_3$/THF mixture (50:50). The aqueous phase was extracted with CH$_2$Cl$_2$ (2×70 mL) and the combined organic extracts were washed with water and brine. The organic phase was dried with K$_2$CO$_3$, filtered through Celite, and evaporated to give crude product. Column chromatography using 5% EtOAc in hexanes gave 1.15 g (73%) of the product which was homogeneous by TLC analysis. $^1$H NMR (300 MHz) δ 4.12-3.91 (m, 1H), 3.79-3.74 (m, 1H), 2.21 (m, 1H), 2.19-1.15 (m, 26H).

trans-2-methyl-6-cyclopentylpiperidine hydrochloride. To a stirred solution of of trans-N-Boc-2-methyl-6-cyclopentylpiperidine (0.84 g. 3.14 mmol) in 115 ml of CH$_2$Cl$_2$ at 0° C. was added dropwise trifluoroacetic acid (7.3 mL, 94.22 mmol). The cooling bath was removed, and stirring was continued for 1 h at room temperature. After concentrating the resulting solution on a rotary evaporator, the remaining liquid was dissolved in ether (40 mL), and 20 ml of water was added. The aqueous phase was extracted with ether (2*10 mL), and the combined organic extracts were washed with saturated NaHCO$_3$ (2*30 mL) and brine. The organic phase was dried over K$_2$CO$_3$, filtered through Celite, and concentrated on a rotary evaporator. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give 0.350 g (55%) of the piperidinium hydrochloride as white needles. mp 166.0-166.9° C.; $^1$H NMR (300 MHz) δ 9.26-9.0 (br d, 2H), 3.67 (s, 1H), 2.99 (s, 1H), 2.31-1.18 (m, 18H); $^{13}$C NMR (75 MHz) δ 52.1 (s), 48.3 (s), 31.5 (s). 28.9 (s), 28.9 (s), 26.9 (s), 25.3 (s), 22.4 (s), 20.8 (s). FT-IR (neat): 3420, 2940, 2867, 1652, 1591, 1456, 1428, 1417, 1176, 1120, 1087, 998, 879. Elemental Analysis for C, $H_{22}$NCl: C, 64.83%; H, 10.90%; N, 6.87%. Found: C, 64.96%; H, 10.94%; N, 6.84%.

N-Boc-Piperidine. A solution of di-tert-butyl dicarbonate (43.7 g, 0.2 mol) in 200 mL of THF was cooled to 0° C. and treated with piperidine (29.7 mL, 0.3 mol) dropwise. The mixture was stirred for 10 min, warned to room temperature, and then stirred for 30 minutes. The mixture was diluted with of 10% sodium bicarbonate solution and extracted with ether. The extracts were washed with brine, and combined extracts were dried over $K_2CO_3$ and then concentrated to give a crude product as an oil. Purification by distillation under reduced pressure afforded 36.1 g (97%) of product as a clear oil which was homogeneous by TLC analysis. $^1$H NMR (250 MHz) δ 3.37-3.33 (br. t, 4H), 1.56-1.44 (m, 15H); $^{13}$C NMR (62.7 MHz) 154.8 (s), 78.9 (s), 44.5 (br. s), 28.4 (s), 25.6 (s), 24.4 (s) ppm.

N-Boc-Piperidine-2-Carboxaldehyde. A solution of N-Boc-Piperidine (6.0 g, 32.4 mmol) in ether (65 mL) was cooled to −60° C. and treated with TMEDA (4.9 mL, 32.4 mmol) followed by sec-BuLi (54.8 mL, 71.2 mmol) dropwise. The mixture was slowly warmed to −20° C. and stirred for 10 min and then cooled to −78° C. The mixture was treated with a solution of DMF (3.8 mL, 48.6 mmol) in 6 mL of ether via syringe, stirred for 10 min, and then quenched with 60 mL saturated ammonium chloride solution. The mixture was warmed to room temperature, and the organic layer was separated. The aqueous layer was extracted three times with ether, and the combined extracts were dried over $K_2CO_3$. The organic layer was concentrated to give a crude product as an orange oil. Purification by column chromatography on silica gel with hexanes:EtOAc (4:1) afforded 4.2 g (67%) of the product as a clear oil which was homogeneous by TLC analysis. $^1$H NMR (300 MHz) δ 9.58 (s, 1H), 4.69-4.51 (br. m, 1H), 4.12-3.85 (br. m, 1H), 2.85 (br. s, 1H), 2.19-2.13 (d, 1H), 1.72-1.23 (m, 15H); $^{13}$C NMR (75 MHz) 201.4 (s), 80.4 (s), 43.0 (br. s), 28.3 (s), 24.7 (s), 23.6 (s), 20.9 (s) ppm.

N-Boc-2-Methyl-Piperidine. A solution of N-Boc-Piperidine (15.0 g, 80.95 mmol) in ether (160 mL) was cooled to −78° C. and treated with TMEDA (15.9 mL, 105.2 mmol) followed by sec-BuLi (85 mL, 105.2 mmol) dropwise. The mixture was stirred for 3 h at −78° C. and then treated with a solution of dimethyl sulfate (15.3 mL, 161.9 mmol) in 65 mL of ether. The mixture was warmed to room temperature and then was diluted with water and extracted with ether. The combined extracts were dried over $K_2CO_3$ and then concentrated to give a crude product as a colorless oil. The product was purified by column chromatography on silca gel with 5% EtOAc/hexane to afford 16.0 g (81%) of product as a clear oil which was homogeneous by TLC analysis. $^1$H NMR (300 MHz) δ 4.33 (m, 1H), 3.92-3.81 (pair of br. d, 1H), 2.81-2.72 (dt, 1H), 1.60-1.36 (m, 15H), 1.09-1.07 (d, 3H); $^{13}$C NMR (75 MHz) 154.9 (s), 78.6 (s), 45.9 (s), 38.6 (s), 29.9 (s), 28.4 (s), 25.6 (s), 18.6 (s), 15.6 (s) ppm.

trans-N-Boc-2-Methyl-6-Piperidinecarboxaldehyde. A solution of N-Boc-2-Methyl-Piperidine (9.4 g, 46.9 mmol) in 94 mL of ether was cooled to −60° C. and treated with TMEDA (7.1 mL, 46.9 mmol) followed by sec-BuLi (49.2 mL, 51.66 mmol) dropwise. The mixture was slowly warmed to −20° C. and stirred for 30 min and then cooled to −78° C. The mixture was treated with a solution of DMF (5.5 mL, 70.44 mmol) in 16 mL of ether via syringe, stirred for 10 min, and then quenched with 75 mL saturated ammonium chloride solution. The mixture was warmed to room temperature, and the organic layer was separated. The aqueous layer was extracted with ether, and the combined extracts were dried over $K_2CO_3$. The organic layer was concentrated to give a crude product as an oil which was chromatographed on silica with hexanes:EtOAc (4:1) to afford 6.5 g (66%) of the trans isomer and 2.1 g (21%) of the cis isomer. Both products were homogeneous by TLC analysis, with the cis isomer positioned just above the trans isomer. $^1$H NMR (250 MHz) δ 9.28-9.26 (d, 1H), 4.25 (br. d, 1H), 3.64-3.57 (m, 1H), 1.74-1.46 (m, 15H), 1.09-1.04 (d, 3H); $^{13}$C NMR (62.7 MHz) 196.3 (s), 155.1 (s), 77.4 (s), 59.2 (s), 47.3 (s), 29.3 (s), 28.2 (s), 25.4 (s), 16.3 (s) ppm.

N-Boc-2-(cis-1-Propenyl)Piperidine. A suspension of ethyltriphenylphosphonium bromide (7.31 g, 19.68 mmol) in 40 mL of THF was cooled to −30° C. and treated with n-BuLi (10.9 mL, 19.68 mmol) dropwise. The deep red solution was slowly warmed to 0° C., stirred for 30 min, and then cooled to −78° C. The ylide was treated with a solution of N-Boc-piperidine-2-carboxaldehyde (3.53 g, 17.89 mmol) in 10 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 1.6 g (41%) of the product which was homogenous by TLC analysis. $^1$H NMR (250 MHz) δ 5.73-5.51 (m, 2H), 5.05-5.01 (m, 1H), 3.98-3.93 (br d, 1H), 2.90-2.81 (m, 1H), 1.7-1.39 (m, 18H); $^{13}$C NMR (62.7 MHz) 154.8 (s), 128.0 (s), 125.8 (s), 79.0 (s), 47.7 (s), 39.6 (s), 30.3 (s), 28.5 (s), 25.6 (s), 19.5 (s), 13.2 (s) ppm.

N-Boc-2-propylpiperidine. A solution of the 1.5 g (6.66 mmol) of V-Boc-2-(cis-1-propenyl)piperdine in 2 mL of ethanol was shaken under 58 psi $H_2$ pressure over 0.3 g Pd/C catalyst overnight, and then the mixture was filtered through Celite and concentrated to give 1.43 g (94%) of the product as a clear colorless oil. No further purification was necessary. $^1$H NMR (250 MHz) δ 4.21-4.17 (br s, 1H), 3.98-3.92 (br d, 1H), 2.79-2.68 (dt, 1H), 1.67-1.23 (m, 19H), 0.93-0.88 (t, 3H); $^{13}$C NMR (62.7 MHz) 155.1 (s), 78.9 (s), 50.0 (s), 38.6 (s), 31.8 (s), 28.4 (s), 25.6 (s), 19.1 (s), 18.9 (s), 14.0 (s) ppm.

N-Boc-2-methyl-6-propylpiperidine. A solution of N-Boc-2-propylpiperidine (1.35 g, 5.94 mmol) was cooled to −60° C. and treated with TMEDA (1.2 mL, 7.66 mmol), followed by sec-BuLi (6.2 mL, 7.66 mmol) dropwise. The mixture was slowly warmed to −20° C., stirred for 30 min, and then cooled to −78° C. The mixture was treated with a solution of dimethyl sulfate (1.1 mL, 11.9 mmol) in ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 1.43 (95.8%) of the product which was homogeneous by TLC analysis. $^1$H NMR (250 MHz) δ 3.94-3.88 (m, 1H), 3.82-3.78 (m, 1H), 1.87-1.21 (m, 21H), 0.93-0.88 (t, 3H); $^{13}$C NMR (62.7 MHz) 155.1 (s), 78.6 (s), 51.3 (s), 46.8 (s), 36.4 (s), 31.8 (s), 28.5 (s), 26.8 (s), 25.6 (s), 23.1 (s), 20.7 (s), 20.1 (s), 19.4 (s), 13.9 (s), 13.7 (s) ppm.

trans-2-methyl-6-n-propylpiperidine hydrochloride. To a stirred solution of the N-Boc-2-methyl-6-propylpiperidine (1.34 g, 5.6 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-methyl-6-propylpiperdine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 124-125.9° C.; $^1$H NMR (300 MHz) δ 9.92 (s, 2H), 3.54 (s, 1H), 3.29 (s, 1H), 2.0-1.2 (m, 13H), 0.91 (t, 3H); $^{13}$C NMR (75 MHz) δ 51.38 (s), 47.82 (s), 32.68 (s), 28.73 (s), 26.14 (s), 18.93 (s), 17.24 (s), 16.69 (s), 13.65 (s) ppm. FT-IR (neat): 3409, 2939, 1591, 1433, 1376, 1183, 1067, 993, 881. MS m/z 142, 141, 140, 126, 98, 84, 81, 70, 55, 44, 41. Elemental Analysis for $C_9H_{20}NCl$: C, 60.81%; H, 11.36%; N, 7.88%. Found: C, 60.72%; H, 11.30%; N, 7.82%.

N-Boc-2-(cis-1-Butenyl)Piperidine. A suspension of propyltriphenylphosphonium bromide (12.01 g, 31.2 mol) in 60 mL of THF was cooled to −30° C. and treated with n-BuLi (12.5 mL, 31.2 mmol) dropwise. The deep red solution was slowly warmed to 0° C., stirred for 30 min, and then cooled to −78° C. The ylide was treated with a solution of N-Boc-piperidine-2-carboxaldehyde (4.1 g, 20.8 mmol) in 10 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 3.3 g (67%) of the product which was homogenous by TLC analysis. $^1$H NMR (250 MHz) δ 5.68-5.39 (m, 2H), 5.01-4.97 (m, 1H), 3.92-3.88 (br d, 1H), 2.87-2.78 (dt, 1H), 2.13-2.06 (m, 2H), 1.64-1.22 (m, 17H), 0.96-0.91 (t, 3H); $^{13}$C NMR (62.7 MHz) 154.6 (s), 133.4 (s), 126.3 (s), 47.8 (s), 39.5 (s), 31.5 (s), 30.6 (s), 28.4 (s), 28.2 (s), 25.5 (s), 22.5 (s), 20.8 (s), 19.4 (s), 14.1 (s) ppm.

N-Boc-2-ButylPiperidine. A solution of N-Boc-2-(1-butenyl)piperdine (3.1, 12.95 mmol) in 6 mL of ethanol was shaken under 58 psi of $H_2$ pressure over 0.62 g Pd/C catalyst overnight, and then the mixture was filtered through Celite and concentrated to give 2.94 (94%) of the product. No further purification was necessary. $^1$H NMR (250 MHz) δ 4.18-4.16 (br s, 1H), 3.96-3.92 (br d, 1H), 2.78-2.69 (dt, 1H), 1.69-1.17 (m, 21H), 0.91-0.86 (t, 3H).

N-Boc-2-Butyl-6-methylPiperidine. A solution of N-Boc-2-butylpiperidine (2.94 g, 12.18 mmol) in 40 mL of ether was cooled to −60° C. and treated with TMEDA (2.4 mL, 15.83 mmol), followed by sec-BuLi (13.0 mL, 15.83 mmol) dropwise. The mixture was slowly warmed to −20° C., stirred for 30 min, and then cooled to −78° C. The mixture was treated with a solution of dimethyl sulfate (2.3 mL, 24.36 mmol) in ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 3.11 (87%) of the product which was homogeneous by TLC analysis. No cis isomer was detected. $^1$H NMR (250 MHz) δ 3.92-3.81 (m, 1H), 3.80-3.79 (m, 1H), 1.66-1.21 (m, 24H), 0.91-0.86 (t, 3H).

trans-2-butyl-6-methylpiperidine hydrochloride. To a stirred solution of the N-Boc-2-butyl-6-methylpiperidine (2.7 g, 10.57 mmol) in 15% trifloroacetic acid (70 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-methyl-6-butylpiperdine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give 1.43 g (71%) of the piperidinium hydrochloride as a white solid. mp 118.0-119.0° C.; $^1$H NMR (250 MHz) δ 9.87 (s, 2H), 3.53 (s, 1H), 3.27 (s, 1H), 2.0-1.2 (m, 15H), 0.90 (t, 3H); $^{13}$C NMR (62.7 MHz) δ 51.57 (s), 47.78 (s), 30.22 (s), 28.78 (s), 26.05 (s), 22.28 (s), 17.24 (s), 16.78 (s), 13.81 (s) ppm. FT-IR (neat): 3430, 2954, 2925, 1584, 1558, 1456, 1418, 1339, 1028, 1009. MS m/z 156, 155, 154, 140, 98, 84, 81, 70, 55, 44, 41. Elemental Analysis for $C_{10}H_{22}NCl$: C, 62.63%; H, 11.59%; N, 7.30%. Found: C, 62.67%; H, 11.52%; N, 7.34%.

N-Boc-2-(cis-1-Heptenyl)Piperidine. A suspension of heptyltriphenylphosphonium bromide (13.0 g, 30.41 mmol) in 60 mL of THF was cooled to −30° C. and treated with n-BuLi (12.2 mL, 30.41 mmol) dropwise. The deep red solution was slowly warmed to 0° C., stirred for 30 min, and then cooled to −78° C. The ylide was treated with a solution of N-Boc-piperidine-2-carboxaldehyde (4.0 g, 20.27 mmol) in 7 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 5.7 g (70%) of the product that was homogeneous by TLC analysis. $^1$H NMR (250 MHz) δ 5.72-5.49 (pair of m, 2H), 5.02-4.96 (br s, 1H), 3.97-3.89 (br d, 1H), 2.89-2.76 (dt, 1H), 2.14-1.99 (m, 2H), 1.61-1.24 (m, 21H), 0.88-0.83 (t, 3H); $^{13}$C NMR (62.7 MHz) 154.6 (s), 133.3 (s), 127.8 (s), 78.9 (s), 48.8 (s), 39.5 (s), 32.3 (s), 30.9 (s), 30.6 (s), 27.6 (s), 25.9 (s), 23.9 (s), 22.5 (s), 21.1 (s), 19.4 (s), 16.9 (s), 14.8 (s), 13.2 (s) ppm.

N-Boc-2-HeptylPiperidine. A solution of N-Boc-2-(1-heptenyl)piperidine (3.92, 13.93 mmol) in 7 mL of ethanol was shaken under 58 psi of $H_2$ pressure over 0.78 g Pd/C catalyst overnight, and then the mixture was filtered through Celite and concentrated to give 3.94 g (quantitative) of the product. No further purification was necessary. $^1$H NMR (250 MHz) δ 4.20-4.15 (br s, 1H), 3.99-3.85 (br d, 1H), 2.79-2.70 (dt, 1H), 1.59-1.25 (m, 21H), 0.89-0.85 (t, 3H); $^{13}$C NMR (62.7 MHz) 155.1 (s), 78.8 (s), 50.3 (s), 38.6 (s), 31.8 (s), 29.6 (s), 29.5 (s), 29.3 (s), 28.4 (s), 26.3 (s), 25.6 (s), 22.6 (s), 18.9 (s), 14.0 (s) ppm.

N-Boc-2-Heptyl-6-methylPiperidine. A solution of N-Boc-2-heptylpiperidine (4.00 g, 14.11 mmol) in 40 mL of ether was cooled to −60° C. and treated with TMEDA (2.8 mL, 18.34 mmol), followed by sec-BuLi (14.1 mL, 18.34 mmol) dropwise. The mixture was slowly warmed to −20° C., stirred for 30 min, and then cooled to −78° C. The mixture was treated with a solution of dimethyl sulfate (3.6 mL, 28.22 mmol) in 13 mL of ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 3.11 (87%) of the product which was homogeneous by TLC analysis. No cis isomer was detected. $^1$H NMR (250 MHz) δ 3.94-3.81 (m, 1H), 3.82-3.80 (m, 1H), 1.70-1.23 (m, 30H), 0.91-0.86 (t, 3H).

trans-2-heptyl-6-methylpiperidine hydrochloride. To a stirred solution of the N-Boc-2-heptyl-6-methylpiperidine (2.7 g, 10.57 mmol) in 15% trifloroacetic acid (70 mL) in dichloromethane was stirred for 2 h at room temperature, and the reaction mixture was quenched with 90 mL saturated NaHCO$_3$ solution. The mixture was extracted with ether *5 and the combined extracts were dried over K$_2$CO$_3$ and then concentrated to give teans-2-methyl-6-heptylpiperdine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 123-125° C.; $^1$H NMR (250 MHz) δ 9.29 (s, 2H), 3.51 (s, 1H), 3.25 (s, 1H), 2.0-1.2 (m, 21H), 0.85 (t, 3H); $^{13}$C NMR (62.7 MHz) 51.7 (s), 47.9 (s), 31.7 (s), 30.7 (s), 29.2 (s), 29.1 (s), 28.8 (s), 26.1 (s), 25.8 (s), 22.5 (s), 17.3 (s), 16.8 (s), 14.0 (s) ppm. FT-IR (neat): 3420, 2956, 2919, 1587, 1470, 1463, 1454, 1393, 1360, 1184, 1125, 890. Elemental Analysis for C$_{13}$H$_{28}$NCl: C, 66.76%; H, 12.09%; N, 5.99%. Found: C, 66.58%; H, 12.06%; N, 6.01%.

trans-N-Boc-2-methyl-6-(2-phenylethenyl)piperidine. A suspension of benzyltriphenylphosphonium bromide (10.3 g, 26.5 mmol) in 54 mL of THF was cooled to −30° C. and treated with n-BuLi (11.2 mL, 26.88 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (4.00 g, 18.93 mmol) in 6 mL of THF, and the mixture was slowly warmed to room temperature. The mixture was diluted with water, and the organic layer was separated. The aqueous layer was extracted with ether and the combined extracts were dried over K$_2$CO$_3$ and then concentrated to give a crude product as an oil. Chromatography on silica with 5% EtOAc/hexane afforded 3.8 g (66%) of the product which was homogeneous by TLC analysis. $^1$H NMR (250 MHz) δ 7.35-7.19 (m, 5H), 6.38-6.34 (m, 1H), 5.80-5.76 (m, 1H), 4.74-4.67, (m, 1H), 4.35-4.18 (m, 1H), 1.80-0.88 (m, 18H).

trans-N-Boc-2-methyl-6-(2-phenylethyl)piperidine. A solution of trans-N-Boc-2-methyl-6-(2-phenylethenyl)piperidine (3.8, 12.54 mmol) in 6 m/L of ethanol was shaken under 58 psi of H$_2$ pressure over 0.70 g Pd/C catalyst overnight, and then the mixture was filtered through Celite and concentrated to give 3.81 g (quantitative) of the product. No further purification was necessary. $^1$H NMR (250 MHz) 87.30-7.14 (m, 5H), 3.93-3.89 (m, 2H), 2.64-2.59 (t, 2H), 1.98-1.20 (m, 20H).

trans-2-methyl-6-(2-phenylethyl)piperidine hydrochloride. To a stirred solution of trans-N-Boc-2-methyl-6-(2-phenylethyl)piperidine (1.4 g, 5.50 mmol) in 15% trifloroacetic acid (35 mL) in dichloromethane was stirred for 2 h at room temperature, and the reaction mixture was quenched with 65 mL saturated NaHCO$_3$ solution. The mixture was extracted with ether *5 and the combined extracts were dried over K$_2$CO$_3$ and then concentrated to give trans-2-methyl-6-(2-phenylethyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 148.3-151.0; $^1$H NMR (300 MHz) δ 9.3, (s, 2H), 7.28-7.11 (m, 5H), 3.43 (s, 1H), 3.19 (s, 1H), 2.67-1.27 (m, 13H); $^{13}$C NMR (75 MHz) 140.0 (s), 128.3 (s), 126.1 (s), 50.9 (s), 47.9 (s), 32.1 (s), 31.5 (s), 28.5 (s), 26.4 (s), 17.2 (s), 16.5 (s). FT-IR (neat): 3410, 3075, 2944, 1590, 1494, 1454, 1435, 1336, 1122, 1029, 751, 701. Elemental Analysis for C$_{14}$H$_{22}$NCl: C, 70.11%; H, 9.27%; N, 5.84%. Found: C, 69.95%; H, 9.19%; N, 5.79%.

N-Boc-2-(cis-1-Ethenyl)Piperidine. A suspension of methyltriphenylphosphonium bromide (10.86 g, 30.41 mmol) in 60 mL of THF was cooled to −30° C. and treated with n-BuLi (13.5 mL, 30.41 mmol) dropwise. The deep red solution was slowly warmed to 0° C., stirred for 30 min, and then cooled to −78° C. The ylide was treated with a solution of N-Boc-piperidine-2-carboxaldehyde (4.0 g, 20.27 mmol) in 10 mL of THF, and the mixture was slowly warmed to room temperature. The mixture was diluted with water, and the organic layer was separated. The aqueous layer was extracted with ether and the combined extracts were dried over K$_2$CO$_3$ and then concentrated to give a crude product as an oil. Chromatography on silica with 5% EtOAc/hexane afforded 2.3 g (55%) of the product which was homogeneous by TLC analysis. $^1$H NMR (250 MHz) δ 5.78-5.67 (m, 1H), 5.16-4.97 (m, 2H), 4.87-4.82 (br s, 1H), 3.95-3.88 (br d, 1H), 2.85-2.74 (dt, 1H), 1.87-1.37 (m, 15H); $^{13}$C NMR (62.7 MHz) 155.3 (s), 136.8 (s), 115.4 (s), 79.2 (s), 52.4 (s), 39.6 (s), 28.5 (s), 28.3 (s), 25.5 (s), 19.4 (s) ppm.

N-Boc-2-ethylpiperidine. A solution of the (2.25 g, 10.65 mmol) of N-Boc-2-(cis-1-ethenyl)piperdine in 3 mL of ethanol was shaken under 58 psi H$_2$ pressure over 0.3 g Pd/C catalyst overnight, and then the mixture was filtered through Celite and concentrated to give 1.78 g (82%) of the product as a clear colorless oil. No further purification was necessary. $^1$H NMR (250 MHz) δ 4.11-4.05 (br s, 1H), 3.97-3.93 (br d, 1H), 2.75-2.66 (dt, 1H), 1.84-1.33 (m, 17H), 0.85-0.80 (t, 3H); $^{13}$C NMR (62.7 MHz) 154.7 (s), 78.8 (s), 51.8 (s), 38.6 (s), 28.4 (s), 28.0 (s), 25.6 (s), 22.5 (s), 18.9 (s), 10.8 (s) ppm.

N-Boc-2-Ethyl-6-methylPiperidine. A solution of N-Boc-2-ethylpiperidine (1.5 g, 7.0 mmol) in 28 mL of ether was cooled to −60° C. and treated with TMEDA (1.6 mL, 10.85 mmol), followed by sec-BuLi (8.5 mL, 10.85 mmol) dropwise. The mixture was slowly warmed to −20° C., stirred for 30 min, and then cooled to −78° C. The mixture was treated with a solution of dimethyl sulfate (1.6 mL, 16.69 mmol) in ether and slowly warmed to room temperature. The mixture was diluted with water and then extracted with ether. The combined extracts were dried over K$_2$CO$_3$ and concentrated to give a crude product as an oil which was chromatographed on silica with 5% EtOAc/hexane to give 0.88 g (59%) of the product which was homogeneous by TLC analysis. $^1$H NMR (250 MHz) δ 3.91-3.87 (m, 1H), 3.69-3.65 (m, 1H), 1.83-1.41 (m, 17H), 1.21-1.19 (d, 3H), 0.85-0.82 (t, 3H); $^{13}$C NMR (62.7 MHz) 155.2 (s), 78.6 (s), 53.0 (s), 46.8 (s), 28.5 (s), 27.2 (s), 26.7 (s), 22.4 (s), 20.7 (s), 13.4 (s), 11.4 (s) ppm.

trans-2-ethyl-6-methylpiperidine hydrochloride. To a stirred solution of the N-Boc-2-ethyl-6-methylpiperidine (0.88 g, 3.87 mmol) in 15% trifloroacetic acid (15 mL) in dichloromethane was stirred for 2 h at room temperature, and the reaction mixture was quenched with 90 mL saturated NaHCO$_3$ solution. The mixture was extracted with ether *5 and the combined extracts were dried over K$_2$CO$_3$ and then concentrated to give teans-2-ethyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 174.9-175.2° C.; $^1$H NMR (250 MHz) δ 9.33 (s, 2H), 3.54 (s, 1H), 3.19 (s, 1H), 2.07-1.46 (m, 13H), 0.99 (t, 3H); $^{13}$C NMR (62.7 MHz) 53.0 (s), 47.9 (s), 28.8 (s), 25.6 (s), 23.8 (s), 17.2 (s), 16.8 (s), 10.2 (s) ppm. FT-IR (neat):

3420, 2931, 1588, 1455, 1393, 1186, 1065, 960. Elemental Analysis for $C_8H_{18}NCl$: C, 58.69%; H, 11.11%; N, 8.55%. Found: C, 58.64%; H, 11.09%; N, 8.56%.

trans-N-Boc-2-methyl-6-(1-propenyl)piperidine. A suspension of ethyltriphenylphosphonium bromide (4.92 g, 13.25 mmol) in 27 mL of THF was cooled to −30° C. and treated with n-BuLi (5.41 mL, 13.25 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (2.00 g, 9.46 mmol) in 3 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 2.26 g (81%) of the product which was homogeneous by TLC analysis. $^1$H NMR (250 MHz) δ (5.51-5.38 (m, 2H), 4.61-4.56 (m, 1H), 4.08 (m, 1H), 1.91-1.19 (m, 21H); $^{13}$C NMR (62.7 MHz) 155.2 (s), 133.5 (s), 122.9 (s), 78.9 (s), 48.8 (s), 47.3 (s), 28.5 (s), 28.3 (s), 27.7 (s), 20.3 (s), 14.7 (s), 12.8 (s) ppm.

trans-2-methyl-6-(1-propenyl)piperidine hydrochloride. To a stirred solution of trans-N-Boc-2-methyl-6-(1-propenyl)piperidine (1.80 g, 7.65 mmol) in 15% trifloroacetic acid (38 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-methyl-6-(1-propenyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid that was homogeneous by TLC analysis. mp 139.5-141.1° C.; $^1$H NMR (250 MHz) δ 9.39 (s, 2H), 5.84-5.86 (m, 2H), 4.23 (s, 1H), 3.54 (s, 1H), 1.9-1.44 (m, 12H); $^{13}$C NMR (62.7 MHz) 131 (s), 123 (s), 48 (s), 28.5 (s), 28 (s), 17.6 (s), 17.1 (s), 13.7 (s) ppm. FT-IR (neat): 3420, 3020, 2944, 1588, 1459, 1434, 1386, 821, 816, 804. Elemental Analysis for $C_9H_{18}NCl$: C, 61.52%; H, 10.35%; N, 7.97%. Found: C, 61.44%; H, 10.29%; N, 7.88%.

trans-N-Boc-2-(1-butenyl)-6-methylpiperidine. A suspension of propyltriphenylphosphonium bromide (5.11 g, 13.25 mmol) in 27 mL of THF was cooled to −30° C. and treated with n-BuLi (6.31 mL, 13.25 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (2.00 g, 9.46 mmol) in 3 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 1.80 g (80%) of the product a clear oil which was homogeneous by TLC analysis. $^1$H NMR (250 MHz) δ 5.48-5.31 (m, 2H), 4.59-4.54 (m, 1H), 4.07-4.00 (m, 1H), 2.12-1.38 (m, 15H), 1.23-1.19 (d, 3H), 0.97-0.95 (t, 3H); $^{13}$C NMR (62.7 MHz) 155.5 (s), 131.9 (s), 130.8 (s), 78.9 (s), 49.0 (s), 47.4 (s), 28.5 (s), 28.2 (s), 27.8 (s), 20.6 (s), 20.2 (s), 14.9 (s), 14.2 (s) ppm.

trans-2-(1-butenyl)-6-methylpiperidine hydrochloride. To a stirred solution of trans-N-Boc-2-(1-butenyl)-6-methylpiperidine (1.80 g, 7.65 mmol) in 15% trifloroacetic acid (38 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-(1-butenyl)-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid that was homogeneous by TLC analysis. mp 167-169.0° C.; $^1$H NMR (250 MHz) δ 9.4 (s, 2H), 5.71-5.58 (m, 2H), 4.17 (s, 1H), 3.54 (s, 1H), 2.2-1.4 (m, 11H), 0.98 (t, 3H); $^{13}$C NMR (62.7 MHz) δ 138.5 (s), 122.4 (s), 48.2 (s), 47.9 (s), 28.74 (s), 28.45 (s), 21.3 (s), 17.6 (s), 16.9 (s), 13.8 (s). FT-IR (neat): 3425, 3183, 3072, 2961, 2915, 1656, 1585, 1463, 1443, 1407, 1107, 1075, 960, 883, 803. Elemental Analysis for $C_{10}H_{20}NCl$: C, 63.29%; H, 10.65%; N, 7.38%. Found: C, 63.14%; H, 10.58%; N, 7.32%.

trans-N-Boc-2-(1-pentenyl)-6-methylpiperidine. A suspension of methyltriphenylphosphonium bromide (5.29 g, 13.25 mmol) in 27 mL of THF was cooled to −30° C. and treated with n-BuLi (6.13 mL, 13.44 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (2.00 g, 9.46 mmol) in 3 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 2.53 g (87%) of the product which was homogeneous by TLC analysis. $^1$H NMR (250 MHz) δ 5.48-5.28 (m, 2H), 4.58-4.54 (m, 1H), 4.06-4.03 (m, 1H), 2.10-1.23 (m, 19H), 1.22-1.18 (d, 3H), 0.93-0.88 (t, 3H), 1H), 4.07-4.00 (m, 1H), 2.12-1.38 (m, 15H), 1.23-1.19 (d, 3H), 0.97-0.95 (t, 3H); $^{13}$C NMR (62.7 MHz) 155.5 (s), 132.4 (s), 129.2 (s), 78.9 (s), 49.1 (s), 47.5 (s), 29.4 (s), 28.5 (s), 28.2 (s), 27.8 (s), 22.8 (s), 20.2 (s), 15.0 (s), 13.9 (s) ppm.

trans-2-(1-pentenyl)-6-methylpiperidine hydrochloride. To a stirred solution of trans-N-Boc-2-(1-pentenyl)-6-methylpiperidine (2.5 g, 9.35 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-(1-pentenyl)-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid that was homogeneous by TLC analysis. mp 150.4-150.9° C.; $^1$H NMR (250 MHz) δ 9.5-9.3 (br. d, 2H), 5.74-5.62 (m, 2H), 4.19 (s, 1H), 3.55 (s, 1H), 2.1-1.3 (m, 13H), 0.87 (t, 3H); $^{13}$C NMR (62.7 MHz) δ 136.8 (s), 123.0 (s), 48.3 (s), 47.9 (s), 29.9 (s), 28.8 (s), 28.4 (s), 22.3 (s), 17.6 (s), 17.1 (s), 13.8 (s). FT-IR (neat): 3424, 3171, 2939, 1635, 1597, 1582, 1459, 1432, 1384, 1287, 1123, 1075, 895. Elemental Analysis for $C_{11}H_{22}NCl$: C, 64.83%; H, 10.9%; N, 6.87%. Found: C, 64.77%; H, 10.82%; N, 6.85%.

trans-N-Boc-2-methyl-6-(1-isopentenyl)piperidine. A suspension of isobutyltriphenylphosphonium bromide (10.58 g, 26.5 mmol) in 42 mL of THF was cooled to −30° C. and treated with n-BuLi (12.2 mL, 26.88 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (4.00 g, 18.93 mmol) in 6 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 3.2 g (63%) of the product which was homogeneous by TLC analysis. $^1$H NMR (250 MHz) δ 5.41-5.14 (m, 2H), 4.62-4.58 (m, 1H), 4.05-4.01 (m, 1H), 2.69-2.68 (m, 1H), 1.90-1.38 (m, 15H), 1.23-1.20 (d, 3H), 0.93-0.87 (t, 6H); $^{13}$C NMR (62.7 MHz) 156.1 (s), 136.8 (s), 129.8 (s), 79.0 (s), 49.1 (s), 47.5 (s), 28.7 (s), 28.5 (s), 27.9 (s), 26.6 (s), 23.3 (s), 23.0 (s), 20.2 (s), 15.1 (s) ppm.

trans-N-Boc-2-methyl-6-isopentylpiperidine. A solution of trans-N-Boc-2-methyl-6-(1-isopentenyl)piperidine (1.5, 5.61 mmol) in 3 mL of ethanol was shaken under 58 psi of $H_2$ pressure over 0.31 g Pd/C catalyst overnight, and then the mixture was filtered through Celite and concentrated to give 1.51 (99%) of the product. No further purification was necessary. $^1$H NMR (250 MHz) δ 3.94-3.87 (m, 1H), 3.81-3.72 (m, 1H), 1.89-1.15 (m, 23H), 0.88-0.85 (d, 6H); $^{13}$C NMR (62.7 MHz) 155.2 (s), 78.6 (s), 51.9 (s), 46.8 (s), 36.3 (s), 32.1 (s), 28.5 (s), 28.0 (s), 26.9 (s), 23.1 (s), 22.7 (s), 22.5 (s), 20.8 (s), 13.6 (s) ppm.

trans-2-methyl-6-isopentylpiperidine hydrochloride. To a stirred solution of trans-N-Boc-2-methyl-6-isopentylpiperidine (1.5 g, 5.56 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-methyl-6-isopentylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 134.1-134.7° C.; $^1$H NMR (250 MHz) δ 9.36 (s, 2H), 3.53 (s, 1H), 3.25 (s, 1H), 1.96-1.1 (m, 14H), 0.88-0.82 (d, 6H); $^{13}$C NMR (62.7 MHz) δ 51.9 (s), 47.8 (s), 34.7 (s), 28.9 (s), 28.4 (s), 27.8 (s), 26.0 (s), 22.7 (s), 22.1 (s), 17.3 (s), 16.9 (s). FT-IR (neat): 3422, 2949, 1636, 1602, 1587, 1500, 1422, 1384, 1230, 1105, 1030, 998, 895. Elemental Analysis for C, $H_{24}NCl$: C, 64.20%; H, 11.78%; N, 6.80%. Found: C, 64.08%; H, 11.72%; N, 6.78%.

trans-2-methyl-6-(1-isopentenyl)piperidine hydrochloride. To a stirred solution of trans-N-Boc-2-methyl-6-(1-isopentenyl)piperidine (1.5 g, 5.56 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-methyl-6-(1-isopentenyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 157.5-156.5° C.; $^1$H NMR (250 MHz) δ 9.37 (br. d, 2H), 5.59-5.46 (m, 2H), 4.19 (s, 1H), 3.59 (s, 1H), 2.66-2.59 (m, 1H), 1.8-1.5 (m, 9H), 1.0 (pair of d, 6H); $^{13}$C NMR (62.7 MHz) δ 143.6 (s), 120.6 (s), 48.3 (s), 47.9 (s), 28.9 (s), 28.6 (s), 27.3 (s), 23.01 (s), 22.6 (s), 17.5 (s), 16.9 (s). FT-IR (neat): 3426, 3188, 3018, 2952, 1625, 1584, 1464, 1359, 1180, 1099, 958, 881. Elemental Analysis for $C_{11}H_{22}NCl$: C, 64.84%; H, 10.91%; N, 6.87%. Found: C, 64.06%; H, 10.77%; N, 6.78%.

trans-N-Boc-2-(1-isohexenyl)-6-methylpiperidine. A suspension of isoamyltriphenylphosphonium bromide (10.95 g, 26.5 mmol) in 42 mL of THF was cooled to −30° C. and treated with n-BuLi (11.9 mL, 26.88 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (4.00 g, 18.93 mmol) in 6 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 2.8 g (56%) of the product which was homogeneous by TLC analysis. $^1$H NMR (250 MHz) δ 5.53-5.32 (m, 2H), 4.56-4.51 (m, 1H), 4.04-4.02 (m, 1H), 1.99-1.37 (m, 18H), 1.23-1.18 (d, 3H), 0.91-0.84 (d, 6H); $^{13}$C NMR (62.7 MHz) 155.5 (s), 132.8 (s), 128.2 (s), 78.9 (s), 49.1 (s), 47.6 (s), 36.4 (s), 28.6 (s), 28.5 (s), 28.0 (s), 27.9 (s), 26.3 (s), 25.6 (s), 22.5 (s), 22.4 (s), 20.7 (s), 20.2 (s), 15.2 (s), 13.6 (s) ppm.

trans-N-Boc-2-isohexyl-6-methylpiperidine. A solution of trans-N-Boc-2-(1-isohexenyl)-6-methylpiperidine (1.35, 4.79 mmol) in 4 mL of ethanol was shaken under 58 psi of $H_2$ pressure over 0.34 g Pd/C catalyst overnight, and then the mixture was filtered through Celite and concentrated to give 1.40 g (quantitative) of the product. No further purification was necessary. $^1$H NMR (250 MHz) δ 3.92-3.90 (m, 1H), 3.79-3.76 (m, 1H), 1.84-1.14 (m, 28H), 0.87-0.82 (d, 6H); $^{13}$C NMR (62.7 MHz) 154.7, 78.6, 51.6, 46.9, 38.9, 34.5, 28.5, 27.9, 26.8, 24.8, 23.2, 22.6, 22.5, 20.8, 13.7 ppm.

trans-2-isohexyl-6-methylpiperidine hydrochloride. To a stirred solution of trans-N-Boc-2-isohexyl-6-methylpiperidine (1.4 g, 5.50 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-isohexyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 155.0-156.0° C.; $^1$H NMR (250 MHz) δ 9.17 (s, 2H), 3.50 (s, 1H), 3.25 (s, 1H), 1.94-1.15 (m, 16H), 0.82 (d, 6H); $^{13}$C NMR (62.7 MHz) δ 51.7 (s), 47.9 (s), 38.4 (s), 30.9 (s), 28.8 (s), 27.8 (s), 26.1 (s), 23.5 (s), 22.5 (s), 22.3 (s), 17.3 (s), 16.8 (s) ppm. FT-IR (neat): 3430, 2948, 1615, 1589, 1557, 1472, 1436, 1418, 1362, 1102, 895. Elemental Analysis for $C_{12}H_{26}NCl$: C, 65.56%; H, 11.95%; N, 6.37%. Found: C, 64.90%; H, 11.89%; N, 6.26%.

trans-2-isohexenyl-6-methylpiperidine hydrochloride. To a stirred solution of trans-N-Boc-2-isohexyl-6-methylpiperidine (1.4 g, 5.50 mmol) in 15% trifloroacetic acid (35 mL) in dichloromethane was stirred for 2 h at room temperature, and the reaction mixture was quenched with 70 mL saturated NaHCO$_3$ solution. The mixture was extracted with ether *5 and the combined extracts were dried over K$_2$CO$_3$ and then concentrated to give trans-2-isohexenyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 164.2-167.0° C.; $^1$H NMR (250 MHz) δ 9.44 (s, 2H), 5.71 (s, 2H), 4.18 (s, 1H), 3.56 (s, 1H), 2.0-1.5 (m, 12H), 0.94 (dd, 6H); $^{13}$C NMR (62.7 MHz) δ 135.7 (s), 123.6 (s), 48.4 (s), 47.9 (s), 36.9 (s), 28.9 (s), 28.4 (s), 28.2 (s), 22.5 (s), 22.1 (s), 17.6 (s), 17.2 (s) ppm. FT-IR (neat): 3429, 3165, 2940, 1620, 1550, 1478, 1400, 1354, 1097, 890. Elemental Analysis for C$_2$H$_{24}$NCl: C, 66.17%; H, 11.13%; N, 6.43%. Found: C, 66.25%; H, 11.05%; N, 6.50%.

trans-2-heptenyl-6-methylpiperidine hydrochloride. To a stirred solution of the N-Boc-2-heptenyl-6-methylpiperidine (1.5 g, 5.08 mmol) in 15% trifloroacetic acid (35 mL) in dichloromethane was stirred for 2 h at room temperature, and the reaction mixture was quenched with 90 mL saturated NaHCO$_3$ solution. The mixture was extracted with ether *5 and the combined extracts were dried over K$_2$CO$_3$ and then concentrated to give teans-2-heptenyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 121.1-122.0° C.; $^1$H NMR (CDCl$_3$) δ 9.44 (s, 2H), 5.68 (m, 2H), 4.19 (s, 1H), 3.56 (s, 1H), 2.2-1.2 (m, 17H), 0.88 (t, 3H); $^{13}$C NMR (CDCl$_3$) δ 137.1 (s), 122.8 (s), 48.34 (s), 47.94 (s), 31.4 (s), 28.8 (s), 28.4 (s), 27.9 (s), 22.4 (s), 17.6 (s), 17.1 (s), 13.97 (s). FT-IR (near): 3435, 3192, 2924, 1586, 1431, 1030, 673. Elemental Analysis for C$_{13}$H$_{26}$NCl: C, 67.34%; H, 11.33%; N, 6.04%. Found: C, 67.44%; H, 11.23%; N, 5.98%.

trans-N-Boc-2-methyl-6-(ethenyl propionyl)piperidine. To a stirred solution of the trans-N-Boc-2-Methyl-6-Piperidinecarboxaldehyde in CH$_2$Cl$_2$ (25 mL), was added ylide (carbethoxymethylene)-triphenylphosphorane (8.24 g, 23.66 mmol). The mixture was stirred at reflux for 2 hours, and another half equivalent of the ylide was added (2 g) in 4 ml CH$_2$Cl$_2$. The mixture was stirred overnight, and was then refluxed for 2 hours more. The mixture was concentrated by evaporation. A small amount of CH$_2$Cl$_2$ was added, and the mixture was immediately purified with column chromatography (silica gel, 5% EtOAc in hexanes) to afford 2.01 g (80%) of the product that was homogeneous by TLC analysis. $^1$H NMR (250 MHz) δ 7.02-6.95 (dd, 1H), 5.83-5.77 (d, 1H), 4.46-4.42 (m, 1H), 4.21-4.09 (m, 3H), 2.03-1.10 (m, 21H); $^{13}$C NMR (62.7 MHz) 166.6 (s), 155.2 (s), 151.1 (s), 119.2 (s), 79.6 (s), 60.1 (s), 59.1 (s), 51.9 (s), 47.2 (s), 29.2 (s), 28.3 (s), 26.7 (s), 26.3 (s), 19.7 (s), 16.2 (s), 14.2 (s) ppm.

trans-N-Boc-2-methyl-6-(ethyl propionyl)piperidine. A solution of trans-N-Boc-2-methyl-6-(ethenyl propionyl)piperidine (2.0 g, 6.70 mmol) in 3 mL of ethanol was shaken under 58 psi of H$_2$ pressure over 0.65 g Pd/C catalyst overnight, and then the mixture was filtered through Celite and concentrated to give 1.8 g (90%) of the product which was homogeneous by TLC analysis. $^1$H NMR (250 MHz) δ 4.16-4.08 (q, 2H), 3.93-3.83 (m, 2H), 2.36-2.28 (t, 2H), 2.04-1.08 (m, 20H); $^{13}$C NMR (62.7 MHz) 155.4 (s), 79.1 (s), 60.3 (s), δ 1.0 (s), 47.2 (s), 31.9 (s), 29.6 (s), 28.5 (s), 26.9 (s), 25.8 (s), 24.2 (s), 20.5 (s), 14.2 (s) ppm.

trans-2-methyl-6-(ethyl propionyl)piperidine hydrochloride. To a stirred solution of trans-N-Boc-2-methyl-6-(ethyl propionyl)piperidine. (1.8 g, 6.01 mmol) in 15% trifloroacetic acid (35 mL) in dichloromethane was stirred for 2 h at room temperature, and the reaction mixture was quenched with 75 mL saturated NaHCO$_3$ solution. The mixture was extracted with ether *5 and the combined extracts were dried over K$_2$CO$_3$ and then concentrated to give trans-2-methyl-6-(ethyl propionyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 121.1-122.0° C.; $^1$H NMR (300 MHz) 89.44 (s, 2H), 5.68 (m, 2H), 4.19 (s, 1H), 3.56 (s, 1H), 2.2-1.2 (m, 17H), 0.88 (t, 3H); $^{13}$C NMR (75 MHz) δ 137.1 (s), 122.8 (s), 48.34 (s), 47.94 (s), 31.4 (s), 28.8 (s), 28.4 (s), 27.9 (s), 22.4 (s), 17.6 (s), 17.1 (s), 13.97 (s) ppm. FT-IR (neat): 3435, 3192, 2924, 1586, 1431, 1030, 673. Elemental Analysis. for C$_{13}$H$_{26}$NCl: C, 67.34%; H, 11.33%; N, 6.04%. Found: C, 67.44%; H, 11.23%; N, 5.98%.

trans-2-methyl-6-(ethenyl propionyl)piperidine hydrochloride. To a stirred solution of trans-N-Boc-2-methyl-6-(ethenyl propionyl)piperidine. (1.8 g, 3.36 mmol) in 15% trifloroacetic acid (35 mL) in dichloromethane was stirred for 2 h at room temperature, and the reaction mixture was quenched with 75 mL saturated NaHCO$_3$ solution. The mixture was extracted with ether *5 and the combined extracts were dried over K$_2$CO$_3$ and then concentrated to give trans-2-methyl-6-(ethenyl propionyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occurred. The solid was collected via filtration, and dried in vacuo to give the piperidinium hydrochloride as a white solid. mp 154.8-156.3; $^1$H NMR (300 MHz) δ 9.89 (s, 2H), 7.03 (dd, 1H), 6.24 (d, 1H), 4.24-4.11 (m, 3H), 3.45 (s, 1H), 2.2-1.49 (m, 9H), 1.26-1.22 (t, 3H); $^{13}$C NMR (75 MHz) 6165.1 (s), 140.1 (s), 126.3 (s), 60.83 (s), 54.3 (s), 51.8 (s), 48.6 (s), 29.4 (s), 27.9 (s), 26.3 (s), 17.9 (s), 14.1 (s) ppm. FT-IR (neat): 3374, 3107, 2943, 1717, 1683, 1635, 1539, 1436, 1312, 1190, 1033, 981. Elemental Analysis for C$_{11}$H$_{20}$NO$_2$Cl: C, 56.52%; H, 8.64%; N, 5.99%. Found: C, 56.37%; H, 8.58%; N, 5.89%.

Biological Activity

Figure 5:
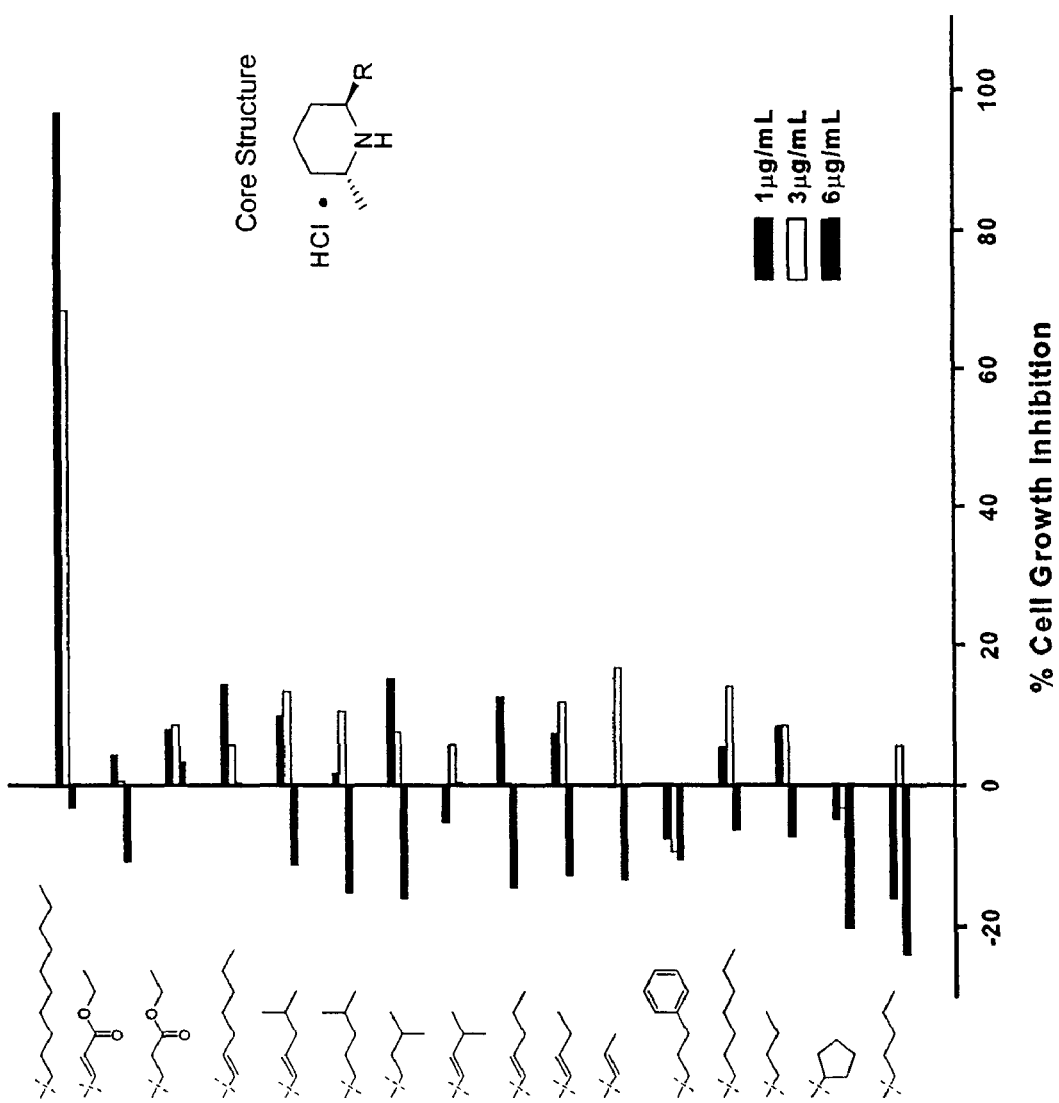

Biological Activity—Anti-Cancer Activity of Compounds According to the Present Invention 10,000 SVR cells were seeded in a 24 well dish [Arbiser, et al., *J. Am. Acad. Derm.*, pp. 925-929 (June, 1999)] and treated with various compounds (or control) according to the present invention at concentrations of 6 μg/ml, 3 μg/ml and 1 μg/ml, respectively (see the table set forth in FIG. 5). The cell numbers were counted at 48 hours.

It is to be understood by those skilled in the art that the foregoing description and examples are illustrative of practicing the present invention, but are in no way limiting. Variations of the detail presented herein may be made without departing from the spirit and scope of the present invention as defined by the following claims.

The invention claimed is:

1. A method of treating a tumor or cancer in a patient in need thereof comprising administering to said patient a pharmaceutical composition in oral, topical or systemic dosage form comprising an effective amount of a compound having the structure:

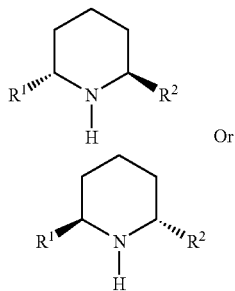

wherein $R^1$ is a methyl group and $R^2$ is an undecyl group or a pharmaceutically acceptable salt thereof, in combination with a pharmaceutically acceptable carrier, additive or excipient, wherein said tumor is selected from the group consisting of neurofibromatosis, tuberous sclerosis and hemangiomas and said cancer is selected from the group consisting of cervical, uterine, anal, ocular, stomach, colon, bladder, rectal, kidney, liver, pancreatic, lung, breast, ovarian, prostate, testicular, renal, brain/cns, head and neck, throat, esophageal, mouth, pharynx, larynx, Ewing's Sarcoma, Kaposi's Sarcoma, melanoma, basal cell carcinoma, small cell lung, squamous cell carcinoma, choriocarcinoma, rhabdomyosarcoma, angiosarcoma, Wilms Tumor, neuroblastoma and lymphoma.

2. The method according to claim 1 wherein said tumor is selected from the group consisting of neurofibromatosis, tuberous sclerosis and hemangiomas and said cancer is basal cell carcinoma or squamous cell carcinoma.

3. The method according to claim 1 wherein said cancer is selected from the group consisting of cervical, uterine, ovarian, anal, ocular, stomach, colon, bladder, rectal, liver, pancreatic, lung, breast, prostate, testis, renal, brain/cns, head and neck, throat, Ewing's Sarcoma, Kaposi's Sarcoma, basal cell carcinoma, squamous cell carcinoma, small cell lung cancer, choriocarcinoma, rhabdomyosarcoma, angiosarcoma, Wilms Tumor, neuroblastoma, mouth/pharynx, esophageal, larynx and lymphoma.

4. The method according to claim 1 wherein said cancer is selected from the group consisting of cervical, anal, ocular, stomach, colon, bladder, rectal, liver, pancreatic, lung, breast, ovarian, prostate, testis, renal, brain/cns, head, neck and throat, mouth/pharynx, esophageal, larynx, kidney and lymphoma.

5. The method according to claim 1 wherein said cancer is selected from the group consisting of Ewing's Sarcoma, Kaposi's Sarcoma, basal cell carcinoma, squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

6. The method according to claim 1 wherein said cancer is selected from the group consisting of cervical, anal, testicular cancer, basal cell carcinoma and squamous cell carcinoma.

7. The method according to claim 1 wherein said cancer is selected from the group consisting of stomach, colon, bladder, rectal, liver, pancreatic, lung, breast, brain/cns, head, neck, throat, mouth, pharynx, larynx, and esophageal.

8. The method according to claim 1 wherein said cancer is selected from the group consisting of cervical, anal, ocular, stomach, colon, bladder, rectal, liver, pancreatic, lung, breast, renal, brain/cns and lymphoma.

9. The method according to claim 1 wherein said basal cell carcinoma or said squamous cell carcinoma is a cutaneous malignancy.

10. The method according to claim 1 wherein said cancer is basal cell carcinoma.

11. The method according to claim 1 wherein said cancer is squamous cell carcinoma.

* * * * *